US008700113B2

(12) United States Patent
Kristensen et al.

(10) Patent No.: US 8,700,113 B2

(45) Date of Patent: Apr. 15, 2014

(54) SENSOR FOR DETECTION OF CARBOHYDRATE

(75) Inventors: Jesper Svenning Kristensen, Virum (DK); Klaus Gregorius, Soborg (DK); Casper Struve, Kongens Lyngby (DK); John Myhre Frederiksen, Kobenhavn V (DK); Yihua Yu, Birkerod (DK)

(73) Assignee: Medtronic Minimed, Inc., Northridge, CA (US)

( * ) Notice: Subject to any disclaimer, the term of this patent is extended or adjusted under 35 U.S.C. 154(b) by 1745 days.

(21) Appl. No.: 11/791,924

(22) PCT Filed: Dec. 7, 2005

(86) PCT No.: PCT/EP2005/013114

§ 371 (c)(1), (2), (4) Date: Feb. 28, 2008

(87) PCT Pub. No.: WO2006/061207

PCT Pub. Date: Jun. 15, 2006

(65) Prior Publication Data

US 2008/0188723 A1 Aug. 7, 2008

(30) Foreign Application Priority Data

Dec. 7, 2004 (GB) .................................. 0426823.1

(51) Int. Cl.
*A61B 5/1455* (2006.01)

(52) U.S. Cl.
USPC ............................ 600/316; 600/310; 600/322

(58) Field of Classification Search
USPC .................................................. 600/309-344
See application file for complete search history.

(56) References Cited

U.S. PATENT DOCUMENTS

| | | | |
|---|---|---|---|
| 4,679,562 | A | 7/1987 | Luksha |
| 5,194,393 | A | 3/1993 | Hugl et al. |
| 5,277,872 | A | 1/1994 | Bankert et al. |
| 5,342,789 | A | 8/1994 | Chick et al. |
| 5,474,915 | A | 12/1995 | Dordick et al. |
| 5,476,776 | A | 12/1995 | Wilkins |
| 5,587,442 | A | 12/1996 | Kiessling et al. |
| 6,002,954 | A | 12/1999 | Van Antwerp et al. |

(Continued)

FOREIGN PATENT DOCUMENTS

| | | | |
|---|---|---|---|
| EP | 0226443 | A1 | 6/1987 |
| EP | 0 561 653 | A1 | 9/1993 |

(Continued)

OTHER PUBLICATIONS

Remy Loris, "Principles of structures of animal and plant lectins", Jun. 19, 2002, Biochimica et Biophysica Acta, 1572,198-208.*

(Continued)

*Primary Examiner* — Eric Winakur
*Assistant Examiner* — Marjan Fardanesh
(74) *Attorney, Agent, or Firm* — Nixon & Vanderhye P.C.

(57) ABSTRACT

A sensor for the detection or measurement of carbohydrate analyte (such as glucose) in fluid comprises components of a competitive binding assay the readout of which is a detectable or measurable optical signal (such as FRET assay) retained by a material that permits diffusion of analyte but not the assay components, the assay components comprising: an animal lectin; and an analyte analogue capable of competing with analyte for binding to the lectin.

27 Claims, 7 Drawing Sheets

(56) References Cited

U.S. PATENT DOCUMENTS

| | | | |
|---|---|---|---|
| 6,107,365 | A | 8/2000 | Bertozzi et al. |
| 6,163,714 | A | 12/2000 | Stanley et al. |
| 6,232,130 | B1 | 5/2001 | Wolf |
| 6,256,522 | B1 | 7/2001 | Schultz |
| 6,271,315 | B1 | 8/2001 | Kiessling et al. |
| 6,383,220 | B1 | 5/2002 | Van Blitterswijk et al. |
| 6,538,072 | B2 | 3/2003 | Kiessling et al. |
| 6,625,479 | B1 | 9/2003 | Weber et al. |
| 6,671,527 | B2 | 12/2003 | Petersson et al. |
| RE38,525 | E | 6/2004 | Stanley et al. |
| 6,927,246 | B2 | 8/2005 | Noronha et al. |
| 6,994,691 | B2 | 2/2006 | Ejlersen |
| 7,045,361 | B2 | 5/2006 | Heiss et al. |
| 7,228,159 | B2 | 6/2007 | Petersson et al. |
| 7,297,548 | B2 | 11/2007 | Kawanishi et al. |
| 2003/0125262 | A1 | 7/2003 | Kiessling et al. |
| 2003/0166136 | A1 | 9/2003 | Bandman et al. |
| 2003/0216300 | A1 | 11/2003 | Cantor et al. |
| 2004/0214190 | A1 | 10/2004 | Butz et al. |
| 2004/0248801 | A1 | 12/2004 | Kiessling et al. |
| 2004/0265898 | A1 | 12/2004 | Afar et al. |
| 2007/0148652 | A1 | 6/2007 | Norrild et al. |
| 2007/0153279 | A1 | 7/2007 | Aasmul |
| 2008/0024779 | A1 | 1/2008 | Aasmul |

FOREIGN PATENT DOCUMENTS

| | | | |
|---|---|---|---|
| EP | 0 594 772 | B1 | 8/1996 |
| EP | 0 856 580 | A1 | 8/1998 |
| EP | 1 247 522 | A1 | 10/2002 |
| JP | 62-234100 | | 10/1987 |
| WO | WO 91/09312 | | 6/1991 |
| WO | WO 93/01498 | | 1/1993 |
| WO | WO 97/19188 | | 5/1997 |
| WO | 98/55869 | | 12/1998 |
| WO | WO 98/55869 | | 12/1998 |
| WO | WO 00/02048 | | 1/2000 |
| WO | 00/16099 | | 3/2000 |
| WO | WO 00/16099 | | 3/2000 |
| WO | 0 505 479 | B1 | 9/2001 |
| WO | WO 02/30275 | A1 | 4/2002 |
| WO | WO 02/46752 | A2 | 6/2002 |
| WO | WO 03/006992 | A1 | 1/2003 |
| WO | WO 03/031578 | | 4/2003 |
| WO | WO 2005/059037 | A1 | 6/2005 |
| WO | WO 2005/110207 | A1 | 11/2005 |

OTHER PUBLICATIONS

Lakowicz, Principles of Fluorescence Spectroscopy, Plenum Press, 1983, Chapter 3.
Tyagi et al, Nature Biotechnology (1998) 18:p. 49.
Russell et al, "Potentially Implantable Fluorescent Glucose Sensor . . . ", presented to American Institute of Chemical Engineers; 2000.
Kilpatrick (2002) Transfus. Med. 12, 335.
Teillet et al, Journal of Immunology, 2005, pp. 2870-2877.
Voss et al, Am. J. Respir. Cell Mol. Biol. vol. 4, pp. 88-94, 1991.
Chang et al, "Molecular Characterization of Human CD94: . . . ", Eur. J. Immunol. 1995, 25:2433-2437.
Kilpatrick et al, "P35, an opsonic lectin of the ficolin family . . . ", Immunology Letters 67 (1999) 109-112.
Itin et al, "ERGIC-53 Is a Functional Mannose-selective . . . ", Molecular Biology of the Cell, vol. 7, 483-493, Mar. 1996.
Christa et al, "High Expression of the human . . . ", Eur. J. Biochem. 267, 1665-1671 (2000).
Arce et al, "The Human C-type Lectin CLECSF8 . . . ", Eur. J. Immunol. 2004, 34:210-220.
Giorgino et al, "The sentrin-conjugating enzyme . . . ", PNAS, Feb. 1, 2000, vol. 93, No. 3, 1125-1130.
Appendices A, B and C of "Handbook of Animal Lectins: Properties and Biomedical Applications", Kilpatrick, Wiley 2000.
Kobayashi et al, 2004, J. Mag. Reson. Imaging, 20(3) 512-518.
Ballerstadt et al, Diabetes Technology & Therapeutics, vol. 6, No. 2, 2004.
Gestwicki et al (2002) Chemistry and Biology 9, p. 163.
Lakowicz, J.R., "Principles of Fluorescence Spectroscopy", 2nd Edition, 1999.
Fakirov et al, Malcromol. Chem. 191 (1990) 603-614.
Ballerstadt et al, "Competitive-binding assay method . . . ", Analytica Chimica Acta 345 (1997) 203-212.
Presanis et al, "Biochemistry and genetics of mannan-binding . . . ", Biochemical Society Transactions (2003), vol. 31, Part 4, pp. 748-752.
Gestwicki et al, J. Am. Chem. Soc., 2002, 124, 14922-14933.
Yang et al, "Synthesis of a multivalent display . . . ", Carbohydrate Research 337 (2002) 1605-1613.
Kanai et al, J. Am. Chem. Soc., 1997, 119, 9931-9932.
Lamanna et al, Journal of Bacteriology, Sep. 2002, p. 4981-4987.
Owen et al, Organic Letters 2002 vol. 4, No. 14, pp. 2293-2296.
Ehwald et al, "Viscosimetric Affinity Assay", Analytical Biochemistry 234, 1-8 (1996).
Beyer et al, "Compensation of Temperature and . . . ", Biotechnol. Prog. 2000, 16, 1119-1123.
Chinnayelka et al, "Resonance Energy Transfer . . . ", Biomacromolecules 2004, 5, 1657-1661.
Montalto et al, "A Keratin Peptide Inhibits . . . ", (2001), J. Immunol, 166, 4148-4153.
Pekari et al, "Synthesis of the Fully . . . ", J. Org. Chem. 2001, 66, 7432-7442.
Bahulekar et al, "Polyacrylamides containing sugar . . . ", Biotechnology Techniques, vol. 12(10) 1998 721-724.
Ballerstadt et al, "A homogeneous affinity . . . ", Sensors and Actuators B 38-39 (1997) 171-175.
Van Damme et al, Handbook of Plant Lectins: Properties and Biomedical Applications, Wiley & Sons, 1998, p. 142.
Hagberg, Journal of Applied Physiology, 1981, vol. 51, pp. 108.
Gordon et al, Nature, 1998, vol. 392, pp. 30-31.
Laursen, Biochemical Society Transaction (2003) vol. 31, part 4.
Kiessling et al, "Chapter 29. Principles for Multivalent Ligand Design", Annual Reports in Medicinal Chemistry, 2000, pp. 321-330.
International Search Report mailed Apr. 6, 2006.
Ballerstadt R. et al.: "Competitive-Binding Assay Method Based on Fluorescence Quenching Ofligands Held in Close Proximity by a Multivalent Receptor," Analytica Chimica Acta, Elsevier, Amsterdam, NL, vol. 345, No. 1-3, 1997, pp. 203-212, XP000901095.
U.S. Appl. No. 11/596,589, filed Nov. 15, 2006.
U.S. Appl. No. 11/792,046, filed Feb. 28, 2008.
Official Action (and English translation) in JP 2007-543804 dated Nov. 24, 2010.

* cited by examiner

SENSOR FOR DETECTION OF CARBOHYDRATE

This application is the U.S. national phase of International Application No. PCT/EP2005/013114 filed 7 Dec. 2005 which designated the U.S. and claims priority to GB 0426823.1 filed 7 Dec. 2004, the entire contents of each of which are hereby incorporated herein by reference.

The present invention relates to a sensor, to a method of preparing the sensor and to a method of using the sensor.

The sensor may be used in the measurement or monitoring of carbohydrate in fluid, for example glucose in body fluid, using optical techniques.

The sensor is particularly suitable for use in situations in which glucose levels must be closely monitored and/or where glucose measurements must be taken repeatedly, such as in diabetes management.

In the management of diabetes, the regular measurement of glucose in the blood is essential in order to ensure correct insulin dosing. Furthermore, it has been demonstrated that in the long term care of the diabetic patient better control of the blood glucose levels can delay, if not prevent, the onset of retinopathy, circulatory problems and other degenerative diseases often associated with diabetes. Thus, there is a need for reliable and accurate self-monitoring of blood glucose levels by diabetic patients.

It is desirable to measure blood glucose over the range of concentrations which may occur in a diabetic patient, that is, from 0 to 35 mM or even higher.

Currently, blood glucose is monitored by diabetic patients with the use of commercially available calorimetric test strips or electrochemical biosensors (e.g. enzyme electrodes), both of which require the regular use of a lancet-type instrument to withdraw a suitable amount of blood each time a measurement is made. On average, the majority of diabetic patients would use such instruments to take a measurement of blood glucose twice a day. However, the US National Institute of Health has recommended that blood glucose testing should be carried out at least four times a day, a recommendation that has been endorsed by the American Diabetes Association. This increase in the frequency of blood glucose testing imposes a considerable burden on the diabetic patient, both in financial terms and in terms of pain and discomfort, particularly in the long-term diabetic who has to make regular use of a lancet to draw blood from the fingertips. Thus, there is clearly a need for a better long-term glucose monitoring system that does not involve drawing blood from the patient.

There have been a number of proposals for glucose measurement techniques that do not require blood to be withdrawn from the patient.

It has been observed that the concentration of analytes in subcutaneous fluid correlates with the concentration of said analytes in the blood, and consequently there have been several reports of the use of glucose monitoring devices which are sited in a subcutaneous location. The use of competitive binding assays for glucose which can be remotely interrogated is of particular interest.

A method of assaying a competitive binding is to use a proximity-based signal generating/modulating moiety pair (discussed in U.S. Pat. No. 6,232,120), which is typically an energy transfer donor-acceptor pair (comprising an energy donor moiety and an energy acceptor moiety). The energy donor moiety is photoluminescent (usually fluorescent).

In such methods, an energy transfer donor-acceptor pair is brought into contact with the sample (such as subcutaneous fluid) to be analyzed. The sample is then illuminated and the resultant emission detected. Either the energy donor moiety or the energy acceptor moiety of the donor-acceptor pair is bound to a receptor carrier, while the other part of the donor-acceptor pair (bound to a ligand carrier) and any analyte present compete for binding sites on the receptor carrier. Energy transfer occurs between the donors and the acceptors when they are brought together, which produces a detectable lifetime change (reduction) of the fluorescence of the energy donor moiety. Also, a proportion of the fluorescent signal emitted by the energy donor moiety is quenched.

The lifetime change is reduced or even eliminated by the competitive binding of the analyte. Thus, by measuring the apparent luminescence lifetime, for example, by phase-modulation fluorometry or time-resolved fluorometry (see Lakowicz, Principles of Fluorescence Spectroscopy, Plenum Press, 1983, Chapter 3), the amount of analyte in the sample can be determined.

It is to be noted that the efficiency of the energy transfer depends on the quantum yield of the donor, the overlapping of the emission spectrum of the donor with the absorption spectrum of the acceptor, and the relative distance and orientation between the donor and the acceptor.

In EP0561653 a method of interrogating a receptor and a ligand as described above, is disclosed.

An example of donor-acceptor energy transfer is fluorescence resonance energy transfer (Foerster resonance energy transfer, FRET), which is non-radiative transfer of the excited-state energy from the initially excited donor (D) to an acceptor (A). The donor typically emits at shorter wavelengths, and its emission spectrum overlaps with the absorption spectrum of the acceptor. Energy transfer occurs without the appearance of a photon and is the result of long-range dipole-dipole interactions between the donor and acceptor.

The term resonance energy transfer (RET) is more correct because the FRET process does not involve the appearance of a photon. However, FRET and RET are often used interchangeably.

An important characteristic of FRET is that it occurs over distances comparable to the dimensions of biological macromolecules. The distance at which FRET is 50% efficient, called the Förster distance, is typically in the range of 20-60 Å. Förster distances ranging from 20 to 90 Å are convenient for competitive binding studies.

Labelling an analyte-binding moiety with a donor (D) and an analyte analogue with an acceptor (A), or vice versa, would create an assay capable of generating a measurable response based on the donor-to-acceptor distance. Thus, binding of the D-“analyte-binding moiety” to A-“analyte analogue” results in a decrease in donor intensity or lifetime. The analyte in the sample competes for the analyte-binding moieties on D-“analyte-binding moiety”, releasing D-“analyte-binding moiety” from the acceptor (A). The intensity decay time and phase angles of the donor are thus expected to increase with increasing glucose concentration.

These principles have been used in glucose sensing by energy transfer.

WO91/09312 describes a subcutaneous method and device that employs an affinity assay based on glucose (incorporating an energy transfer donor-acceptor pair) that is interrogated remotely by optical means. Examples WO97/19188, WO00/02048, WO03/006992 and WO02/30275 each describe glucose sensing by energy transfer, which produce an optical signal that can be read remotely.

A person skilled in the art will appreciate that the acceptor could be a fluorophore. Any fluorescent signal emitted by the energy acceptor moiety following excitation with a beam of incident radiation at a wavelength within the absorption spectrum of the energy acceptor moiety is unaffected by the FRET process. It is therefore possible to use the intensity of the fluorescent signal emitted by the energy acceptor moiety as an internal reference signal, for example in continuous calibration of the sensor or to monitor the extent to which the sensor has degraded and thus indicate the need to implant or inject a fresh sensor. The fall of this signal below an acceptable baseline level would indicate the need to implant or inject a fresh sensor.

The energy acceptor moiety may, however, be a non-fluorescent dye. In this case a compound with fluorescence quenching capability is used instead of the specific energy acceptor moiety. An example of a powerful and non-specific fluorescence quencher is given by Tyagi et al. Nature Biotechnology (1998) 18: p 49.

The systems discussed above rely on Concanavalin A (Con A) as the glucose binding moiety. Concanavalin A is a lectin. The term "lectin" includes any carbohydrate-binding protein not obviously involved in carbohydrate metabolism and which does not belong to any of the major classes of immunoglobulins. Lectins show selective binding to carbohydrates via carbohydrate recognition domains (CRDs). Lectins occur naturally in both monomeric and multimeric forms, the latter often comprising a number of subunits, each bearing several CRDs.

Concanavalin A is not stable for long periods under assay conditions. Experiments by the inventors (see Example 8) suggest that Concanavalin A is stable at body temperature for less than 20 days.

Also, Concanavalin A is toxic and potentially immunogenic (however, it is used in glucose assays in small quantities which are thought to be safe in the human body).

It has also been suggested that sweet pea and lentil lectins could be used as glucose binding moieties in such systems ("A Potentially Implantable Fluorescent Glucose Sensor Based on Molecular Recognition in Poly(ethylene glycol) Hydrogels", Ryan J. Russell et al., presented to American Institute of Chemical Engineers). However, these lectins are expected to have similar disadvantages to Con A.

U.S. Pat. No. 6,232,130 discloses an assay in which low valency lectins ("carbohydrate binding ligands") are used. These have 3 or fewer CRDs. The assay uses an analyte analogue ("glycoconjugate") comprising a carbohydrate, a label (e.g. a FRET component) and a carrier molecule. The carrier molecule may be a protein (e.g. bovine serum albumin, BSA) or a synthetic polymer.

The present inventors have appreciated that there is a need to find carbohydrate binding moieties which have good stability and which do not have the disadvantages associated with Con A. They have investigated the use of alternative carbohydrate binding moieties. Surprisingly, they have found that animal lectins, including human lectins, can be used as carbohydrate binding moieties.

Accordingly, in a first aspect, the present invention provides a sensor for the detection or measurement of carbohydrate analyte in fluid, the sensor comprising components of a competitive binding assay the readout of which is a detectable or measurable optical signal retained by a material that permits diffusion of the analyte but not the assay components, the assay components comprising:

an animal lectin; and an analyte analogue capable of competing with carbohydrate for binding to the lectin.

Preferably, the analyte is a monosaccharide. In a preferred embodiment, the analyte is glucose.

Preferably, the sensor is suitable for the detection or measurement of glucose in body fluid, for example subcutaneous fluid. It is desirable for the sensor to be suitable for use in vivo, and this is discussed in more detail below.

Preferably, the analyte analogue is capable of competing with glucose at physiological calcium concentrations. Typical physiological calcium concentrations are in the range of 1.15 to 1.29 mM.

Detection

Suitable detection techniques include FRET, fluorescence energy transfer, fluorescence polarisation, fluorescence quenching, phosphorescence, luminescence enhancement, luminescence quenching, diffraction or plasmon resonance.

The binding assay generating the optical signal should preferably be reversible such that a continuous monitoring of fluctuating levels of analyte can be achieved. This reversibility is a particular advantage of the use of a binding assay format in which the components of the assay are not consumed.

Preferably, the detectable or measurable optical signal is generated using a proximity based signal generating/modulating moiety pair. A signal is generated or modulated when a first member of the pair is brought into close proximity with a second member of the pair.

Preferably, the proximity based signal generating/modulating moiety pair is an energy donor moiety and energy acceptor moiety pair. Energy donor moieties and energy acceptor moieties are also referred to as donor and acceptor chromophores respectively. An energy acceptor which does not emit fluorescence is referred to as a quenching moiety.

In this case, the lectin is labelled with one of an energy donor and energy acceptor moiety pair and the analyte analogue is labelled with the other of the energy donor and energy acceptor moiety pair.

The most preferred embodiment of the sensor of the invention incorporates an assay which generates an optical readout using the technique of FRET.

Where the assay is to be used in vivo, it is desirable for donors to fluoresce at 550 to around 700 nm and for acceptors to absorb light at around 650 nm. This avoids overlap between the donor fluorescence and in vivo autofluorescence at lower wavelengths.

Alexa Fluor 594™ (e.g. as succinimidyl ester) is an energy donor moiety with a suitable emission spectrum for use in vivo. This dye absorbs at 594 nm and fluoresces at 620 nm.

The HMCV dyes described in WO05/059037 are suitable energy acceptor moieties for use in the invention. These dyes are stabilised carbenium ions. An example is Hexa-Methoxy-Crystal Violet succinimidyl ester (HMCV-1).

Alternatively, QSY 21™ may be used as an energy acceptor moiety with Alexa Fluor 594™ as an energy donor moiety.

Fluorescence lifetime or fluorescence intensity measurements may be made. Fluorescence lifetime may be measured by phase modulation techniques (discussed below).

In a preferred embodiment, the lectin is labelled with AlexaFluor 594 as energy donor moiety, the analyte analogue is labelled with HMCV-1 as energy acceptor moiety, and fluorescence lifetime is measured by phase modulation techniques.

The material retaining the assay components preferably provides sufficient space for the energy donor and the energy acceptor moieties to separate when not bound to one another so that energy transfer can cease.

Lectin

Preferably, the lectin provides a stable signal in the assay for at least 10 days, more preferably for at least 14 days. It is particularly preferable that a stable signal is provided when the sensor is implanted in the human body.

Surprisingly, the present inventors found that MBL was stable in a glucose assay for at least 17 days (see Example 8). Earlier accounts reported a biological half-life for MBL of 4-7 days (Kilpatrick (2002) Transfus. Med. 12, 335).

Preferably, the lectin is a C-type (calcium dependent) lectin.

Preferably, the animal lectin is a vertebrate lectin, for example a mammalian lectin, more preferably a human or humanized lectin. However, it may alternatively be a bird lectin, fish lectin or an invertebrate lectin such as an insect lectin.

Suitably, the lectin is a human lectin derived from the human body. Alternatively, the lectin may be a recombinantly manufactured lectin.

As a further alternative, the lectin may be a humanised animal lectin, for example a humanised bovine lectin. This applies where there is a corresponding human lectin. The lectin may be humanised in an analogous way to antibodies.

Suitably, the lectin is in multimeric form. Multimeric lectins may be derived from the human or animal body. Alternatively, the lectin may be in monomeric form. Monomeric lectins may be formed by recombinant methods or by disrupting the binding between sub-units in a natural multimeric lectin derived from the human or animal body. Examples of forming monomeric lectins by disrupting the binding between sub-units in a natural multimeric lectin are described in U.S. Pat. No. 6,232,130.

Preferably, the lectin has three or more CRDs. More preferably, the lectin has 6 or more CRDs.

Preferably, the lectin is a collectin (collagen-like lectin). These are C-type animal lectins which have collagen like sequences (Gly-Xaa-Yaa triplet). MBL is a C-type collectin whereas Concanavalin A is a C-type lectin. Monomeric collectin CRDs can be prepared by the action of collagenase.

Preferably, the lectin is mannose binding lectin, conglutinin or collectin-43 (e.g. bovine CL-43) (all serum collecting) or a pulmonary surfactant protein (lung collectins).

Mannose binding lectin (also called mannan binding lectin or mannan binding protein, MBL, MBP), for example human MBL, has proved particularly interesting. MBL is a collagen-like defence molecule which comprises several (typically 3 to 4 (MALDI-MS), though distributions of 1 to 6 are likely to occur (SDS-PAGE)) sub-units in a "bouquet" arrangement, each composed of three identical polypeptides. Each sub-unit has a molecular weight of around 75 kDa, and can be optionally complexed with one or more MBL associated serine proteases (MASPs). Each polypeptide contains a CRD. Thus, each sub-unit presents three carbohydrate binding sites. Trimeric MBL and tetrameric MBL (which are the major forms present in human serum, Teillet et al., Journal of Immunology, 2005, page 2870-2877) present nine and twelve carbohydrate binding sites respectively.

MBL occurs naturally in the body as part of the innate immune system where it binds mannose moieties coating the surface of bacteria. Human MBL is not toxic and is non-immunogenic to humans. MBL of other species is expected to be immunogenic but not toxic to humans.

Human MBL is commercially available both in a form derived from the human body and in a recombinantly manufactured form. It is used as a replacement therapy in the treatment of MBL deficient patients who are believed to have increased susceptibility to infectious diseases.

Suitably, the lectin is MBL substantially in trimeric and/or tetrameric form. As explained above, trimeric MBL and tetrameric MBL are believed to be the major naturally occurring multimeric forms in human serum.

Alternatively, the lectin may be a pulmonary surfactant protein selected from SP-A and SP-D. These proteins are similar to MBL. They are water-soluble collecting which act as calcium dependent carbohydrate binding proteins in innate host-defence functions. SP-D also binds lipids. SP-A has a "bouquet" structure similar to that of MBL (Kilpatrick D C (2000) Handbook of Animal Lectins, p. 37). SP-D has a tetrameric "X" structure with CRDs at each end of the "X".

Other suitable animal lectins are those set out in the following list:

- PC-lectin (US 20030216300, US 20040265898)
- CTL-1 (US 179528/10)
- Keratinocyte membrane lectins (Parfuemerie und Kosmetik 74, 164-80)
- CD94 (Eur J Immunol 25, 2433-7)
- P35 (synonym: human L-ficolin, a group of lectins) (Immunol Lett 67, 109-12)
- ERGIC-53 (synonym: MR60) (Mol Biol Cell, 7, 483-93)
- HIP/PAP (Eur J Biochem 267, 1665-71)
- CLECSF8 (Eur J Immunol 34, 210-20)
- DCL (group of lectins) (Appl no 00231996/US)
- GLUT family proteins, especially GLUT1, GLUT4 and GLUT11 (PNAS 97, 1125-30)

Further suitable animal lectins are set out in Appendices A, B and C of "Handbook of Animal Lectins: Properties and Biomedical Applications", David C. Kilpatrick, Wiley 2000.

The lectin is preferably labelled as discussed above. More preferably, the lectin is labelled with an energy donor moiety.

Analyte Analogue

Preferably, the analyte analogue comprises a plurality of carbohydrate or carbohydrate mimetic moieties which bind to binding sites of the lectin. The term "carbohydrate" includes sugars.

Suitable carbohydrate mimetic moieties include peptides such as keratin peptide (SFGSGFGGGY) which mimics N-acetyl glucosamine. It has been shown that keratin peptide can inhibit MBL (Mantacto et al. 2001 J. Immunol. 166, 4148-4153).

It has been found by the inventors that the affinity of common carbohydrate moieties for MBL is as follows: D-Mannose, N-acetyl-D-mannosamine, D-fructose, D-leucrose, erlose, N-acetyl-D-glucosamine, L-Fucose>myo-inositol, D-glucose, D-arabinose, D-palatinose, D-turanose, D-sorbitol, D-ribose, D-tagatose>D-lyxose>lactose, L-arabinose, D-galactose.

Whilst they do not wish to be bound by this theory, the inventors believe that strong binding to MBL and other lectins is the result of binding at a number of sites. The binding at each site is relatively weak (low affinity) but the cumulative effect is strong binding (high avidity). Thus, an analyte analogue which does not bind all the binding sites is more readily displaced by analyte, which binds all the binding sites, than an analyte analogue which does bind all the binding sites. This explains why an analyte analogue containing mannose, which has a higher affinity for MBL than does glucose, can be displaced by glucose.

The parameters which affect avidity of an analyte analogue for a given lectin are:

- number of carbohydrate or carbohydrate mimetic moieties;
- affinity of the carbohydrate or carbohydrate mimetic moieties for the lectin;
- calcium concentration (at least for MBL); and
- flexibility of the analyte analogue.

Physiological calcium concentration cannot be controlled. However, the other parameters can be selected to give an analyte analogue with an appropriate measurement range.

The effect of analyte analogue flexibility on assay performance has not previously been identified or addressed.

Previously disclosed analyte analogues (e.g. those of U.S. Pat. No. 6,232,130) have comprised globular proteins to which carbohydrate and energy donor or energy acceptor moieties are conjugated. In such molecules the carbohydrate and energy donor or energy acceptor moieties have fixed positions. This means that the analyte analogues cannot necessarily adopt a conformation which allows binding of a plurality of carbohydrate moieties to lectin CRDs.

Also, the relative positioning of the carbohydrate and energy donor or energy acceptor moieties in such analyte analogues may not allow optimum interaction between the energy donor and acceptor moieties when the analyte analogue and lectin are bound. This will affect FRET and weaken the optical signal.

Finally, these analyte analogues often do not bind to lectins at physiological calcium concentrations. The calcium concentration required for optimum binding of mannose glycoconjugates to MBL has been found to be around 20 mM.

These insights have been used by the inventors to develop various analyte analogues which have different avidity for the same lectin, and which can therefore be used to measure carbohydrate concentration over different ranges.

Preferably, the assay is capable of measuring blood glucose for concentrations over at least part of the range of 0 to 35 mM glucose, for example over the range of 0 to 25 mM glucose. Suitably, the $IC_{50}$ value is around 15 mM glucose. More preferably, the assay is capable of measuring glucose concentrations over the range of 2 to 10 mM glucose. A dosage-response curve which is as close as possible to linear within this range is desirable.

Three different types of structure for the analyte analogue are of particular interest.

Carbohydrate-Protein Conjugate or Carbohydrate-Dendrimer Conjugate

First, the analyte analogue may be a carbohydrate-protein conjugate or a carbohydrate-dendrimer conjugate. In either of these cases, carbohydrate mimetic moieties may be used instead of or in addition to carbohydrate moieties.

Examples of suitable carbohydrates for use in such conjugates are monosaccharides and oligosaccharides.

Suitable monosaccharides are optionally derivatised tetroses, pentoses, hexoses, heptoses or higher homologous aldoses or ketoses, for example optionally derivatised D-glucose, D-mannose, N-acetyl-D-glucosamine, L-fucose, D-fructose, D-tagatose or D-sorbitol.

Suitable oligomers may be linear or branched homooligomers or mixed oligomers, for example containing from 2 to 50 carbohydrate units.

The preferred glycosylation is 1→6 or 1→2, as 1→3 and 1→4 glycosylation is expected to interrupt MBL binding. For example, nona(1→6)-α-glucose (dextran 1500 Da) is expected to have higher avidity for MBL than 1,3-β-D-glucoses (e.g. laminanarihexaose). Suitable oligosaccharides include pannose, maltose, maltotriose, isomaltotriose, D-leucrose, erlose, D-palatinose, D-turanose or 1 to 250 kDa dextran (preferably 1 to 40 kDa dextran, for example 1 kda, 1.5 kDa, 5 kDa, 6 kDa, 10 kDa, 12 kDa, 20 kDa, 25 kDa or 40 kDa dextran).

Preferably, the analyte analogue comprises at least one carbohydrate moiety selected from D-fructose, D-leucrose, N-acetyl-glucosamine, D-mannose, L-fucose, N-acetyl-mannosamine, D-arabinose, myo-inositol, D-tagatose, erlose, D-glucose, D-palatinose, D-turanose, D-ribose, D-sorbitol.

More preferably, the analyte analogue comprises at least one glucose moiety and/or at least one N-acetyl glucosamine moiety and/or at least one mannose moiety, since these have a high affinity for MBL and other animal lectins. It is believed that these moieties bind to binding sites of the lectin via their C3 and C4 hydroxyl groups.

Examples of a synthetic branched saccharide are dendrimer "wedges" used to construct dendrimers (e.g. TRIS derived trisaccharide with an amine linker, shown below). Such "wedges" could be conjugated onto a protein such as HSA (human serum albumin), for example via a bifunctional amine linker.

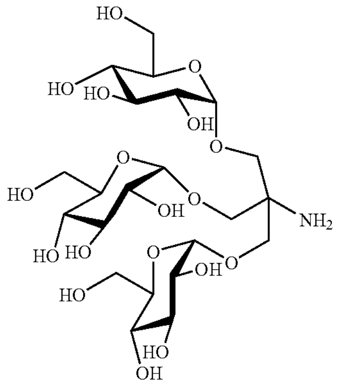

Preferred proteins for use in the conjugate are human proteins having a molecular weight of at least 10 kDa, preferably at least 20 kDa. Preferably, the protein has a non-globular overall tertiary structure. It is believed that this assists binding at more than one binding site, leading to high avidity. Monoclonal antibodies such as herceptin and Remicadem (an immunoglobulin having several globular domains with a non-globular "Y"-shaped overall tertiary structure) are suitable. Other alternative suitable proteins are human thrombin, human lactoferrin and Factor XIII.

As another example of a carbohydrate-protein conjugate, the protein may be a lectin-derived protein, for example a lectin with the CRDs removed.

Suitably, the conjugate may be a carbohydrate-albumin conjugate. For example, the conjugate may be a mannose-HSA conjugate or a mannose-BSA (bovine serum albumin) conjugate. However, conjugates of this type are not preferred since, as mentioned above, binding to MBL has been found to be dependent on calcium concentration. At physiological calcium concentrations a 70 kDa mannose-HSA conjugate with 20 mannose residues was found not to bind MBL. The dependence on calcium concentration decreases with increasing mannosylation.

The skilled person would be aware of synthetic routes to conjugates of this type. As an example, N-isothiocyanato-4-aminophenyl-O-α-D-mannopyranoside (Man-ITC) can be conjugated onto HSA.

Dendrimers for use in the invention preferably have amine-functionalised, carboxylic acid-functionalised or hydroxyl-functionalised surfaces. Preferably, the dendrimers are of the polyamidoamine (PAMAM) or polypropylenimine (DAB) type. Preferably, the molecular weight is less than 60 kDa, for example around 2 to 10 kDa. Such dendrimers can be cleared by the kidney (Kobayashi et al., 2004, J. Mag. Reson. Imaging 20(3) 512-518).

Polysaccharide

Second, the analyte analogue may be an optionally derivatised polymer of carbohydrate and/or carbohydrate mimetic moieties (both included in the term "polysaccharide" used herein). Dextran (a glucose polymer, poly(1→6)-α-glucose) binds strongly to MBL and similar lectins. The inventors believe that this is a result of the large number of glucose residues (approximately 430 residues in 70 kDa dextran) and the flexibility of dextran. The concentration of glucose needed to displace dextran from MBL is therefore high.

A glucose assay based on dextran and MBL can optimally measure glucose concentrations of around 30 mM. This is much higher than the normal 5 mM glucose concentration in blood. Such an assay can measure glucose concentrations from 0 to 10 mM with a sensitivity of only about one third of the total phase response (0.25° Phase shift per mM Glc, see Example 7).

The present inventors therefore looked for alternative analyte analogues which would bind MBL and similar lectins less strongly, so that more than one third of the total phase response would be available in the 0 to 10 mM glucose range.

The inventors discovered that treating dextran with periodate (which oxidatively cleaves the glucose pyranose ring between the 2 and 3 or 3 and 4 carbons to form a dialdehyde) can be used to reduce the avidity of dextran for MBL and similar lectins. This appears to be because MBL binds to the 3 and 4 equatorial hydroxyls of glucose as explained above. The 3 and 4 hydroxyl groups could inactivated in other ways (for example by oxidation, reduction, alkylation, substitution, glycosylation or esterification).

Very surprisingly, the inventors found that periodate treated dextran-MBL binding is not prevented by physiological calcium concentrations. This is in contrast to mannose-HSA conjugate MBL binding as discussed above. It would have been expected that periodate-treated dextran MBL binding was prevented by physiological calcium concentrations, particularly since the glucose moieties of dextran have lower affinity for MBL than do mannose moieties.

Theoretically two equivalents of periodate per glucose unit could be consumed (one per diol). However, it has been found that 1 to 100 equivalents of periodate is suitable for 70 kDa dextran.

Treatment of the dialdehyde with ammonia or an amine followed by reduction (e.g. with sodium cyanoborohydride) can be used to give an aminated dextran. A procedure can also be used in which the dialdehyde is aminated followed by optional catalytic hydrogenation to yield the free amine. Benzylamine is a useful amine in this context as the intermediate before hydrogenation is a dextran derivative with lipophilic moieties. Also, a benzylamine derived aminated dextran can be used to assess the degree of periodate cleavage using spedtrophotometric techniques. If the benzyl group is removed by catalytic hydrogenation, energy donor or energy acceptor moieties can be coupled to the remaining amine.

Alternatively, a polysaccharide-based analyte analogue can be synthesised which bears different carbohydrate or carbohydrate mimetic moieties of different affinity for MBL and similar lectins. Derivatisation of dextran with mannose moieties to adjust the glucose detection range in a Concanavalin A FRET assay is disclosed in Ballerstadt et al., Diabetes Technology & Therapeutics, vol. 6, no. 2, 2004.

Galactose binds to MBL with very low affinity. Therefore, an analyte analogue containing galactose moieties (for example galactose-derivatised dextran) has lower avidity for MBL than the underivatised analyte analogue.

N-acetyl-glucosamine has a high affinity for MBL. Therefore, an analyte analogue containing N-acetyl-glucosamine moieties (for example GlcNAc derivatised amylose) would have higher avidity for MBL than the underivatised analyte analogue.

Preferably in this embodiment, the analyte analogue is selected from optionally derivatised dextran, mannan, amylose, amylopectin, glycogen, hyaluronate, chondroitin, heparin, dextrin, inulin, xylan, fructan and chitin. As galactose has very low affinity for MBL, a non-derivatised polymer of galactose such as agarose is not preferred as an analyte analogue.

The skilled person would be aware of ways in which a polysaccharide can be derivatised with carbohydrate moieties. As an example, amine-functionalised polysaccharides (for example aminodextran, which is commercially available from CarboMer, San Diego, Calif., USA, Cat. No. 5-00060 or Molecular Probes, Eugene, Oreg., USA, Cat No. D1862) or the aminated dextrans referred to above may conveniently be derivatised. Alternatively, alcohol groups in the polysaccharide and amine groups in the carbohydrate or carbohydrate mimetic moieties may be linked using divinylsulphone. Methods of derivatising dextran are disclosed in EP 594772.

Examples of suitable carbohydrate moieties for derivatisation of polysaccharides are those set out in connection with carbohydrate-protein and carbohydrate-dendrimer conjugates above.

Synthetic Polymer

Third, the analyte analogue may be a synthetic polymer.

Synthesis of an artificial polymer rather than derivatisation of a protein or polysaccharide allows the parameters of the polymer (for example molecular flexibility, water solubility, molecular weight, nature of carbohydrate or carbohydrate mimetic moieties, number of carbohydrate or carbohydrate mimetics moieties, number of proximity based signal generating/modulating moieties) to be readily controlled to improve assay performance. Compared with a polysaccharide, a synthetic polymer has the advantage that the number of carbohydrate moieties can be controlled independently of the length of the polymer. Furthermore, using non-ring containing monomers such as 2-hydroxyethyl acrylate (HEA) in the polymer gives increased molecular rotational flexibility compared with dextran.

Without wishing to be bound by this theory, the inventors believe that it is important that proximity based signal generating/modulating moieties are close to the binding moiety to generate a strong signal. Globular ligands concentrate binding moieties and proximity based signal generating/modulating moieties on a spherical surface so that they are close. In dextran, which is linear, the backbone consists of binding moieties, and consequently it is not possible to control whether binding is close to or remote from a proximity based signal generating/modulating moiety. This can be controlled in the synthetic polymer by positioning the binding moieties close to the proximity based signal generating/modulating moieties.

Preferably in this embodiment, the analyte analogue is a non-saccharide flexible water-soluble polymer bearing pendant carbohydrate or carbohydrate mimetic moieties.

The term "flexible" includes polymers which are capable of significant intermonomeric rotation. Preferably, the polymers do not contain bulky groups (for example ring structures, tert-butyl groups or other sterically large groups) other than the pendant carbohydrate or carbohydrate mimetic moieties and proximity based signal generating/modulating moieties. Preferably, such polymers have very few double bonds in the backbone structure (for example less than 10%). Suitably, such polymers do not have a globular tertiary structure, although they may have such a structure.

Preferably, the polymer is unbranched (unlike the dendrimers discussed above). This improves flexibility of the polymer. However, the polymer may be branched or cross-linked to some extent provided that this does not lead to formation of a hydrogel. For example, 1 to 5 branchings in a polymer with an overall molecular weight of 100 kDa is acceptable.

The term "water soluble" includes polymers having a water solubility at room temperature of at least 4 mg/ml, preferably at least 25 mg/ml, more preferably at least 50 mg/ml, for example at least 100 mg/ml. The solubility will be higher at body temperature. It is important that the polymer is water soluble so that it will dissolve in interstitial fluid when used in a sensor in the body as discussed below. The polymer should be water soluble even when bound to a carbohydrate binding molecule such as MBL.

Preferably, the polymer includes no more than 1 to 5 types of monomer unit, more preferably no more than 3 monomer units.

Suitably, the polymer is a co-polymer comprising first monomer unit residues bearing pendant carbohydrate or carbohydrate mimetic moieties and second monomer unit residues bearing pendant proximity based signal generating/modulating moieties. Alternatively or additionally, a single monomer unit residue bearing both pendant carbohydrate or carbohydrate mimetic moieties and pendant proximity based signal generating/modulating moieties may be used. The use of first and second monomer units is preferred, since the amounts of carbohydrate or carbohydrate mimetic moieties and proximity based signal generating/modulating moieties can then be controlled independently.

Preferably, the co-polymer is a random co-polymer. However, it may also be an alternating co-polymer. Use of a block co-polymer with large blocks is not preferred. However, a block co-polymer with blocks of low molecular weight (for example 1 to 3 kDa) may be used.

Preferably, when used in an assay with MBL as a carbohydrate binding molecule, the polymer binds to MBL at 0 mM glucose at least 50% as strongly as aminodextran, more preferably at least as strongly as aminodextran, but is more easily inhibited. It is particularly desirable that the polymer is easily inhibited (large proportion of total phase response) over the range of 0 to 35 mM glucose, and especially over the range of 2 to 15 mM. This provides an assay over glucose concentrations of particular physiological interest which is more sensitive than a similar assay using aminodextran as a glucose analogue.

More than one type of monomer unit residue bearing carbohydrate or carbohydrate mimetic moieties may be present. The carbohydrate or carbohydrate mimetic moieties may be different, with different affinities for MBL and similar lectins.

Suitably, the first monomer units (or single monomer units) are each a double bond-containing derivative of a carbohydrate or carbohydrate mimetic moiety. However, the first monomer units (or single monomer units) may each be a double bond-containing molecule containing a functional group to which the carbohydrate or carbohydrate mimetic moiety can be linked, suitably after polymerisation.

Preferably, the double bond-containing derivative of the carbohydrate or carbohydrate mimetic moiety is an allyl or vinyl containing derivative of a carbohydrate or carbohydrate mimetic moiety. Other suitable double bond-containing derivatives of carbohydrate or carbohydrate mimetic moieties include homologues of allyl derivatives, for example 3-butenyl or 4-pentenyl derivatives, or styrene derivatives with the carbohydrate or carbohydrate mimetic moiety at the 4 position. Further suitable double bond-containing derivatives of carbohydrate or carbohydrate mimetic moieties include HEA, 2-hydroxyethyl methacrylate (HEMA) or vinyl alcohol (VA) based derivatives.

The carbohydrate or carbohydrate mimetic moieties may be linked to amine, acid, alcohol and/or sulphone functional groups of the first monomer units (or single monomer units). For example, alcohol groups in the monomer units and amine groups in the carbohydrate or carbohydrate mimetic moieties may be linked using divinylsulphone. Where the carbohydrate is mannose, the linkage should not be via the C3-OH or C4-OH groups, since these are important in binding to MBL. In this case, divinylsulphone linkage may be inappropriate.

Amino derivatised carbohydrate moieties can be produced by reductive amination of disaccharides. This allows the carbohydrate moiety to be linked at its anomeric position (Cl).

The carbohydrate or carbohydrate mimetic moiety could be connected to alcohol groups (e.g. in HEA) by Fischer glycosidation.

It is not necessary for the first monomer units (or single monomer units) to contain double bonds.

Examples of suitable carbohydrates for use in the co-polymer are as discussed in connection with Carbohydrate-Protein Conjugates above.

Suitably, the second monomer units (or single monomer units) are each a double bond-containing molecule containing a functional group to which the proximity based signal generating/modulating moiety can be linked, suitably after polymerisation. Suitable functional groups include acid, alcohol and/or sulphone. Linkage after polymerization helps to minimize loss of the expensive proximity based signal generating/modulating moieties.

However, the second monomer units (or single monomer units) may contain the proximity based signal generating/modulating moieties. In this case, the discussion above of suitable polymerisable groups and linkages applies.

In a preferred embodiment, the second monomer units are each N-(3-aminopropyl)methacrylamide or a derivative thereof.

In a preferred embodiment, the single monomer units are each a double bond containing, carbohydrate or carbohydrate mimetic moiety containing derivative of lysine. An example is shown below (multistep reaction scheme):

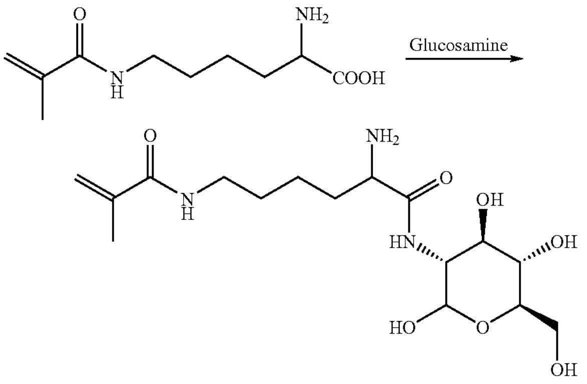

The starting material in this reaction scheme is methacryloyl-L-lysine, available through PolysSciences Europe (Eppelheim, Germany). After polymerization, the alpha amine group could be linked to the proximity based signal generating/modulating moiety.

Preferably, the polymer further contains third monomer unit residues which do not bear pendant carbohydrate or carbohydrate mimetic or proximity based signal generating/modulating moieties. This helps to increase flexibility.

Flexibility is increased by using third monomer units which are sterically unhindered such as HEA. Flexibility is also increased by using third monomer units which are uncharged. A polymer containing no third monomer units would have a large number of positively charged ammonium groups which would need to be inactivated to minimize decreased flexibility because of electrostatic repulsion.

More than one type of third monomer can be included in the polymer.

Preferably, the third monomers units are each a double bond-containing molecule containing a hydrophilic group, for example a hydroxyl group. It is not preferred for the third monomers units to be a lipophilic double bond-containing molecule, for example styrene.

In a preferred embodiment, the third monomer units are each HEA, vinyl pyrrolidone, MMA, HEMA, vinyl alcohol and/or ethylene glycol. However, the skilled person will appreciate that there are many other double bond-containing molecules containing hydrophilic groups which could be used.

Suitably, the monomer units are reacted by addition polymerization. The addition polymerization may be free-radical initiated, for example using potassium peroxodisulfate (PPS) or another peroxide compound.

Other possibilities are condensation polymerization (for example ionic condensation polymerization), ring opening polymerization and atom transfer radical polymerization (ATRP). The skilled person will appreciate that the nature of the monomer units will depend on the desired method of polymerization (for example double bond containing monomer units are not necessary for condensation polymerization).

Suitably, the monomer units are mixed before initiator is added.

Preferably, the polymerization reaction takes less than two days. The length of the polymerization can be used to control the molecular weight of the co-polymer product.

Suitably, the polymerization reaction takes place under oxygen-free conditions.

Suitably, the polymerization reaction is carried out at room temperature.

Where no single monomer units are used, the first monomer units are preferably present in the reaction mixture in an amount of 20 to 70 wt %, more preferably in an amount of 30 to 50 wt %.

Where the third monomer units are used, they are preferably present in the reaction mixture in an amount of 5 to 15 wt %.

It will be appreciated that the composition of the polymer does not exactly reflect the amounts of monomer units present in the reaction mixture. This is because of the influence of other factors (for example steric hindrance and solubility).

It should also be noted that the analyte analogue may consist of two or more separate entities which together act as an analyte analogue. In particular, the analyte analogue may consist of a first entity with at least two analyte analogue moieties and a second entity which is an analyte binding molecule such as a lectin. For example, acceptor labelled MBL and donor labelled MBL can be used together with unlabelled dextran or unlabelled synthetic polymer as a template to bring the donor labelled MBL and acceptor labelled MBL in proximity of each other so that FRET occurs. (example using Con A given by Gestwicki et al. (2002) *Chemistry and Biology* 9, p 163).

The analyte analogue is preferably labelled with one or more proximity based signal generating/modulating moieties as discussed above. Preferably, the analyte analogue comprises one or more energy acceptor moieties (for example HMCV-1 or Alexa Fluor 594™, discussed above). However, it may also comprise one or more energy donor moieties.

The proximity based signal generating/modulating moieties may be attached to the analyte analogue as discussed in connection with the carbohydrate or carbohydrate mimetic moieties above. For example, labelling of dextran can be achieved by direct divinylsulphone coupling or by amination (as described above) followed by coupling. Where an amine derivatised dextran is used as the analyte analogue, care must be taken to avoid cross linking during attachment of the proximity based signal generating/modulating moieties, as this could lead to undesirable precipitation. Methods of derivatising dextran with DVS in order to minimize cross-linking are discussed in EP594772.

The analyte analogue should have a molecular weight high enough to prevent escape from the sensor but low enough that precipitation does not occur when the analyte analogue binds to the lectin. Analyte analogues having a weight in the range of 25 to 250 kDa, more preferably 40 to 250 kDa, more preferably still 70 to 150 kDa, highly preferably 100 to 120 kDa, for example 110 kDa are preferred. Analyte analogues based on 110 kDa dextran are particularly preferred.

Optionally, the analyte analogue and lectin are tethered together.

Sensor Construction

Preferably, the components of the assay are retained by a material which has a pore size that permits diffusion of analyte but not the assay components. However, this selectivity may be achieved in other ways, for example by using a material which allows diffusion of uncharged materials.

Preferably, the components of the assay are retained by a shell or matrix material. The analyte analogue and/or lectin may be grafted onto this material. More preferably, the material is biodegradable as described in WO00/02048. Optionally, the sensor may comprise small particles retained by a shell of biodegradable material as described in WO03/006992.

In a preferred embodiment, the components of the assay are retained by a shell of biodegradable material encapsulating the assay components whilst allowing glucose to contact the assay components, and the biodegradable material comprises a co-polymer having hydrophobic and hydrophilic units, as described in WO2005/110207.

One or more assay component chambers may be present within the shell.

Preferably, the co-polymer is a random copolymer.

Preferably, the co-polymer has a permeability of at least $5.0\times10^{-10}$ $cm^2/s$.

The word "permeability" is used to refer to the overall permeability of analyte (glucose) through hydrated co-polymer which can be measured experimentally.

Preferably, once implanted in the body the co-polymer degrades over a period of one week to one year, for example 30 days. For a typical polymer thickness of 5 μm this corresponds to a degradation rate of 0.17 μm/day.

Preferably, for mobility of glucose, the biodegradable material has a molecular weight cut-off limit of no more than 25000 Da. More preferably, the biodegradable material has a molecular weight cut-off limit of no more than 10000 Da.

Preferably, the weight fraction of the hydrophobic units is from 10 to 90% of the co-polymer, more preferably from 10 to 50% of the co-polymer.

Preferably, the molecular weight of each hydrophilic unit is from 200 to 10000 Da, more preferably from 400 to 4000 Da.

Preferably, the hydrophilic units of the co-polymer each comprise an ester of polyethylene glycol and a diacid. As an alternative to polyethylene glycol, a mixed polymer of ethylene glycol and propylene glycol may be used, and/or the polyether backbone may be substituted with hydrophobic and/or hydrophilic groups. As a further alternative to polyethylene glycol, poly-tetrahydrofuran (poly-THF) may be used.

Preferably, the hydrophilic units comprise terephthalic acid and/or succinic acid as diacids. Other suitable diacids are oxalic acid, tartaric acid, phthalic acid, aspartic acid, malonic acid and oligomeric or polymeric diacids, for example poly (dimer acid-sebacic acid). In one preferred embodiment, the diacid is terephthalic acid only. In an alternative preferred embodiment, the molar ratio of terephthalic acid to succinic acid is 1:2 to 2:1, suitably 1:1.

Alternatively, the hydrophilic units of the co-polymer may comprise oligomers. Suitable oligomers are oligomers of hydroxyethylmethacrylate (HEMA), vinylpyrrolidone, vinyl alcohol, carbohydrates, ethylene oxide and/or 2-acrylamido-2-methyl propane sulfonic acid. Where the hydrophilic units comprise HEMA, biodegradable linkages (for example ester linkages such as terephthalate linkages) are provided within the polymer to increase biodegradability.

Preferably, the molecular weight of each hydrophobic unit is from 400 to 5000 Da.

Preferably, the hydrophobic units of the co-polymer comprise an ester of butane-1,4-diol and a diacid. As an alternative to butane-1,4-diol, pentane-1,5-diol or hexane-1,6-diol may be used.

Preferably, the hydrophobic units comprise terephthalic acid and/or succinic acid as diacids. In a preferred embodiment, the molar ratio of terephthalic acid to succinic acid is 1:2 to 2:1, suitably 1:1. Alternatively, the hydrophobic units comprise terephthalic acid only as diacid. Other suitable diacids are given above.

Alternatively, the hydrophobic units of the co-polymer can comprise oligomers of methylmethacrylate (MMA), polyurethane and/or amides (for example Nylon-6, oligo-N-tertiary butylacrylamide or oligo-N-isopropylacrylamide). Where the hydrophobic units comprise MMA, biodegradable linkages (for example ester linkages such as terephthalate linkages) are provided within the polymer to increase biodegradability.

Preferred polymers have the general formula aPEG(T/S)bPB(T/S)c where "a" denotes the molecular weight of the PEG chain, "b" the weight fraction of the PEG(T/S) (polyethylene glycol terephthalate/succinylate) in the resulting polymer and "c" the weight fraction of the PB(T/S) (polybutylene terephthalate/succinylate) in the resulting polymer. Examples of such polymers are 600PEGT80PBT20, 1000PEGT80PBT20, 2000PEGT80PBT20, 4000PEGT80PBT20, 1000PEGT50PBT50 and 1000PEG(T/S)60PB(T/S)40(T/S 50%). The polymers are biodegradable, have high glucose permeability and have molecular weight cut-off properties at around 25000 Da.

Some of these polymers are disclosed in U.S. Pat. No. 6,383,220 and EP1247522.

The envelope of co-polymer preferably has a thickness of 1 to 50 μm.

In a second aspect, the present invention relates to a method of preparing a sensor as described herein.

Chemical methods for the preparation of polymer microcapsules include phase separation (coacervation), solvent evaporation and/or extraction.

Suitable physical methods for the preparation of polymer microcapsules include spray drying, spray coating, spray chilling, rotary disk atomisation, fluid bed coating, coextrusion (for example stationary nozzle coextrusion, centrifugal head coextrusion, or submerged nozzle coextrusion) and pan coating.

Sensor Use

In a third aspect, the present invention relates to a method of detecting glucose using a sensor as described herein, comprising implantation of the sensor into the skin of a mammmal, detection or measurement of glucose using external optical means.

In a fourth aspect, the present invention relates to a method of detecting glucose using a sensor as claimed described above, comprising detection or measurement of glucose using external optical means by illumination of a said sensor present in or below the skin of a mammal.

Preferably, the method further comprises degradation of biodegradable material in the sensor.

The sensor may be introduced within the skin by injection, preferably using a syringe, or by other methods, in particular by any method described in WO00/02048. The sensor is preferably of a size suitable for injection through a narrow gauge needle to minimise the discomfort to the patient. Preferably, the sensor has a maximum dimension of 20 μm to 1 mm. However, a rod-shaped sensor having a larger maximum dimension may be used.

The sensor may be introduced within the thickness of the dermis, or subdermally, or may be introduced to the epidermis, although in the latter case it would be likely to be expelled from the skin by outgrowth of the epidermal layers, possibly before the biodegradable material has degraded.

Because the sensor is located within the skin, an optical signal generated in the sensor is preferably detected transcutaneously (i.e. through the higher layer(s) of the skin) thus obviating the need for any direct connection between the sensor and the external environment which may lead to infection.

However, detection may alternatively take place via a hollow or transparent means (for example a needle or optical fibre) which allows the sensor to be illuminated by external optical means without passing light through the skin.

Once the sensor is in place in a cutaneous location glucose measurements can be taken as often as is necessary with no adverse effects. This is a particular advantage in relation to the long-term care of diabetic patients because if glucose measurements are taken more frequently, tighter control can be maintained over the level of glucose in the blood and the risk of developing conditions related to poorly regulated blood glucose, such as retinopathy, nephropathy, neuropathy, general micro- and macrovascular damage and poor circulation, will be reduced.

Because the sensor of the invention does not itself contain any of the optical components required to interrogate the readout of the assay (these being preferably provided separately and located outside the body) the sensor can easily be provided in a form which is injectable with minimal discomfort to the patient.

Sensors incorporating an assay employing the technique of FRET may be interrogated by supplying incident radiation at a wavelength within the absorption spectrum of the energy donor moiety and measuring the intensity of the emitted fluorescence or the lifetime of the excited state. Commonly known methods are:

1. Steady state measurement

2. Time-domain lifetime measurement a. Single photon counting b. Streak camera c. Gated detection (pulse sampling)

d. Up-conversion

3. Frequency domain lifetime measurement a. Phase-modulation fluorometry (heterodyne detection)

b. Phase sensitive detection (homodyne detection)

Further description of the principles may be found in Lakowicz, J. R. "Principles of Fluorescence Spectroscopy, Second Edition", 1999.

The preferred method for interrogating the assay is phase-modulation fluorometry.

A suitable optical set-up for interrogating the assay (FIG. 6) consists of a light-emitting diode (LED) 11, which emits light within the emission spectrum of the energy donor moiety. The LED is operated by a driver circuit 13, which modulates the LED at a frequency which results in a sufficient phase shift, preferably in the range of 45°. For a fluorophore with a lifetime of 3 ns, the preferred frequency is 50 MHz. The light emitted by the LED is filtered by an excitation filter 15 and directed towards the sensor 16 by a dichroic beam splitter 17 and focused onto the sensor/skin above the injected sensor 16 by a lens 19. The fluorescence emitted by the sensor is collected by the lens 19. The light passes through the dichroic beam splitter and is filtered through an emission filter 21. The filtered light is focused by a lens 23 onto the detector 25, in this case an avalanche photodiode (APD). The APD is reverse biased by an APD bias supply 27, which is controlled by a signal processing and control unit 29. The signal from the APD is amplified by a trans-impedance amplifier 31, filtered by a bandpass filter 33 and sampled by a first analog-to-digital converter (ADC) 35. Correspondingly, the modulated drive signal to the LED is sampled by a second ADC 37. The signal sampled on the first ADC 35 is:

$$Y_1(t)=A_1*\sin(2*\pi*f*t+\phi_{f1}+\phi_1)$$

$A_1$ is the amplitude of the detected signal from the assay, f is the modulation frequency, $\phi_{f1}$ is the phase lag introduced by the donor fluorophore and $\phi_1$ is a fixed phase lag introduced by the electronic and optical set-up.

The signal sampled on the second ADC 37 is:

$$Y2(t)=A_2*\sin(2*\pi*f*t+\phi_2)$$

$A_2$ is the amplitude of the modulated drive signal to the LED and $\phi_2$ is a fixed phase lag introduced by the electronic set-up The signal processing and control unit derives the phase lag $\phi_{f1}$ introduced by the energy donor moiety by comparing the two sampled signals and compensating for the fixed and known phase lags introduced by the electronics and optics.

Measurements are taken by holding the fluorometer close to the skin and in alignment with the sensor. The phase lag is converted to analyte concentration by the use of a phase-to-analyte-calibration function, such as $$\text{analyte concentration}=A+Bx/(k+x),$$

where A is the phase at no analyte present, B is the phase at maximal response, x is the measured phase, and k is the dissociation constant between the receptor and the analyte analogue.

An alternative measurement technique is measurement of fluorescence intensity.

In this case, the optical means should supply a first beam of incident radiation at a wavelength within the absorption spectrum of the energy donor moiety and preferably a second beam of incident radiation at a wavelength within the absorption spectrum of the energy acceptor moiety (this applies where the energy acceptor moiety is also a fluorophore). In addition, the optical means should preferably be capable of measuring optical signals generated in the sensor at two different wavelengths; wavelength 1 within the emission spectrum of the energy donor moiety (the signal generated in connection with the measurement of analyte) and wavelength 2 in the emission spectrum of the energy acceptor moiety (which could be the analyte signal or the internal reference or calibration signal).

The fluorometer separately measures the following parameters:

At wavelength 1 (energy donor moiety)

Excitation light intensity, I(1,0)

Ambient light intensity, I(1,1)

Intensity of combined fluorescent and ambient light, I(1,2)

At wavelength 2 (energy acceptor moiety)

Excitation light intensity, I(2,0)

Ambient light intensity, I(2,1)

Intensity of combined fluorescent and ambient light, I(2,2)

Again, measurements are taken by holding the fluorometer close to the skin and in alignment with the sensor. When making transcutaneous measurements of the fluorescent signals generated in the sensor it is necessary to take account of the absorption of signal by the skin. The absorptivity of human skin is found by experiment to be lowest in the range from 400 nm to 900 nm. The final output provided is the normalised ratio between the fluorescent intensity from the two fluorophores, defined by the following relation (Equation 1):

$$\text{Final output}=(I(1,2)-I(1,1))*I(2,0)/(I(2,2)-I(2,1))*I(1,0) \quad (1)$$

The final output from the optical means (e.g. the fluorometer) as given by Equation 1 above is converted to analyte concentration preferably by means of a computer using calibration data which can be obtained based on the principles set out in WO00/02048.

Further Aspects of Invention

In a fifth aspect, the present invention relates to a sensor for the detection or measurement of carbohydrate analyte in fluid, the sensor comprising components of a competitive binding assay the readout of which is a detectable or measurable optical signal retained by a material that permits diffusion of analyte but not the assay components, the assay components comprising:

a lectin; and an analyte analogue comprising optionally derivatised dextran in which the 3- and/or 4-hydroxyl groups of at least one of the glucose units have been inactivated, the analyte analogue being capable of competing with analyte for binding to the lectin. Preferably, the dextran is periodate-treated dextran.

In a sixth aspect, the present invention relates to a sensor for the detection or measurement of carbohydrate analyte in fluid, the sensor comprising components of a competitive binding assay the readout of which is a detectable or measurable optical signal retained by a material that permits diffusion of analyte but not the assay components, the assay components comprising:

a lectin; and an analyte analogue comprising a mannose-protein conjugate capable of competing with analyte for binding to the lectin.

Preferably, the mannose-protein conjugate is one prepared using a molar ratio of mannose to HSA in the range of 10:1 to 150:1, for example 15:1, 30:1, 60:1 or 120:1.

In a seventh aspect, the invention relates to a sensor for the detection or measurement of a carbohydrate analyte in fluid, the sensor comprising components of a competitive binding assay the readout of which is a detectable or measurable optical signal retained by a material that permits diffusion of the analyte but not the assay components, the assay components comprising:

a carbohydrate binding molecule labelled with one of a proximity based signal generating/modulating moiety pair; and a carbohydrate analogue capable of competing with the analyte for binding to the carbohydrate binding molecule, the carbohydrate analogue being a flexible water-soluble polymer comprising:

polymerized residues of first monomer units, the first monomer unit residues bearing pendant carbohydrate or carbohydrate mimetic moieties and pendant moieties which are the other of the proximity based signal generating/modulating moiety pair; and/or co-polymerised residues of second monomer units and third monomer units, the second monomer unit residues bearing pendant carbohydrate or carbohydrate mimetic moieties and the third monomer unit residues bearing pendant moieties which are the other of the proximity based signal generating/modulating moiety pair.

In an eighth aspect, the invention relates to a method of producing a polymer as described above, comprising one of the following procedures:

a) polymerising monomer units each bearing a pendant carbohydrate or carbohydrate mimetic moiety and a pendant proximity based signal generating/modulating moiety and optionally third monomer units;

b) co-polymerising first monomer units each bearing a pendant carbohydrate or carbohydrate mimetic moiety and second monomer units each bearing a pendant proximity based signal generating/modulating moiety and optionally third monomer units;

c) polymerising monomer units each bearing a pendant carbohydrate or carbohydrate mimetic moiety and a pendant functional group for linking to an proximity based signal generating/modulating moiety and optionally third monomer units, then reacting the monomer unit residues with the proximity based signal generating/modulating moieties;

d) co-polymerising first monomer units each bearing a pendant carbohydrate or carbohydrate mimetic moiety and second monomer units each bearing a pendant functional group for linking to an proximity based signal generating/modulating moiety and optionally third monomer units, then reacting the second monomer unit residues with the proximity based signal generating/modulating moieties;

e) polymerising monomer units each bearing a pendant functional group, for linking to a carbohydrate or carbohydrate mimetic moiety and a pendant different functional group for linking to an proximity based signal generating/modulating moiety and optionally third monomer units, then reacting the monomer unit residues with the carbohydrate or carbohydrate mimetic moieties and proximity based signal generating/modulating moieties; or f) co-polymerising first monomer units each bearing a pendant functional group for linking to a carbohydrate or carbohydrate mimetic moiety and second monomer units each bearing a pendant different functional group for linking to an proximity based signal generating/modulating moiety and optionally third monomer units, then reacting the first monomer unit residues with the carbohydrate or carbohydrate mimetic moieties and the second monomer unit residues with proximity based signal generating/modulating moieties.

Features described in connection with any aspect of the invention can be applied to other aspects of the invention.

The invention will be further illustrated with reference to examples, and to the Figures in which.

EXAMPLES

General

Figure 1:
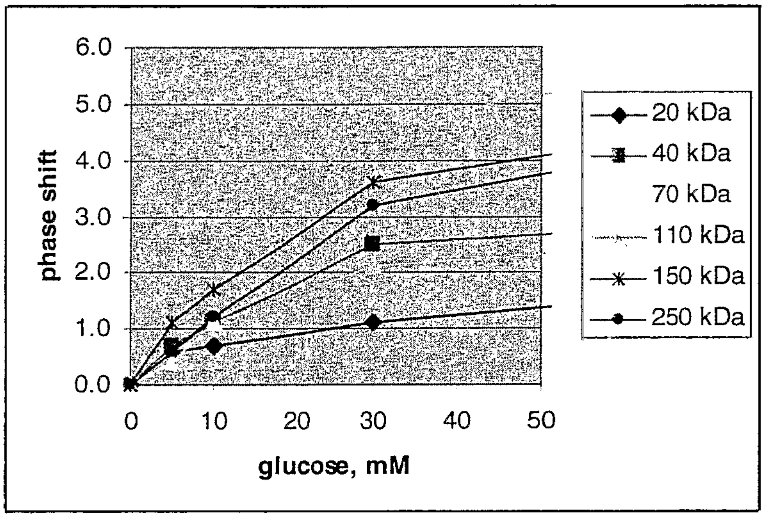
FIG. 1 shows the glucose dose response from a human MBL and dextran assay system for various dextran molecular weights (Example 6).

The following materials were used:

p-Aminophenyl-α-D-mannopyranosyl isothiocyanate, Bovine serum albumin-α-D-mannopyranosyl isothiocyanate (23 eq Man pr. BSA), Human serum albumin, sodium periodate, Biotin-N-hydroxy succinimide, o-phenylene dihydrochloride, benzylamine, ammonia, sodium cyanoborohydride (Sigma-Aldrich).

Nunc F96 MaxiSorp plate (Nunc, Denmark).

PD-10 columns, Streptavidin-HRP (Amersham bioscience).

Dextrans (Pharmacosmos, Denmark).

Mannan binding lectin (available from several sources e.g. Statens Serum Institute, Copenhagen, Denmark)

Dialysis tube Spectra/Por (Spectrum Laboratories Inc., California, USA). Float-A-Lyzer™ 25.000 MWCO dialysis tubing was from Spectrum Laboratories Europe (Breda, The Netherlands).

Sorbitan monooleate (Span® 80), Azodiisobutyrodinitrile (AIBN) and 2-hydroxyethylacrylate were from Sigma-Aldrich. N-(3-aminopropyl)methacrylamide hydrochloride was from PolysSciences Europe (Eppelheim, Germany). 2,2'-Azobis[2-(2-imidazolin-2-yl)propane]dihydrochloride (VA-044) was from Wako GmbH (Neuss, Germany).

Allyl α-D-Glucopyranoside and Allyl 2-acetamido-2-deoxy-α-D-glucopyranoside were from Glycon Biochemicals, Germany. Allyl α-D-Galactopyranoside was from Sigma-Aldrich.

PBS is 20 mM Phosphate, 150 mM NaCl, pH 7.4, and TBS is 20 mM TRIS, 150 mM NaCl, 1.25 mM $CaCl_2$, pH 7.4 unless otherwise stated.

Abbreviations: MBL, Mannan Binding Lectin; PBS, Phosphate buffered saline; TBS, TRIS buffered saline; ELLA, Enzyme Linked Lectin Assay.

Example 1

Staining of MBL

Human MBL was buffer changed (by dialysis) to a 10 mM $NaHCO_3$ buffer containing 150 mM NaCl and 1.25 mM $Ca^{2+}$, pH 8.7. The dye used for staining was Alexa Fluor™ 594 succinimidyl ester (AF594-SE) (Molecular Probes, Eugene, Oreg., USA). The dye was dissolved in dry DMSO and added slowly (10 min.) to the MBL in bicarbonate buffer. Reaction was allowed to take place for 1 hour. The staining was performed with 15 times molar excess (with respect to the polypeptide unit) of dye. Purification was carried out by dialysis against 10 mM Tris buffer pH 7.4, 150 mM NaCl and 1.25 mM $Ca^{2+}$. The obtained degree of labelling of the stained protein was determined by UV spectroscopy as 2.3 dyes per subunit of MBL.

Example 2

Preparation of Dextran 150 kDa Dextran (6.00 g, 0.4 μmol) was dissolved in 250 mM $K_2HPO_4$ pH 11.5 (600 mL). Sodium borohydride (3 g, 0.08 mol) was added followed by the addition of divinylsulfone (15 ml, 0.15 mol). The reaction mixture was stirred for 30 min at RT, before neutralization to pH 7.2 with conc. HCl. After 30 min stirring, the resulting mixture was dialysed (MWCO 10-12 kDa) in water (3×25 L). The contents were transferred to an Erlenmeyer flask and 24% ammonia (200 mL) was added. After 2 h, the pH was adjusted to 10.5, and the reaction was stirred overnight. Excess ammonia was removed by dialysis (MWCO 10-12k) in water (8×25 L), and the entire contents were lyophilised to yield the aminodextran 5.75 g (78%, based on an aminodextran MW of 185 kDa) as a white fluffy substance. Elemental analysis was used to make a rough estimate of the molecular weight, amine incorporation, and amount of incorporated divinylsulfone. (Found C, 39.86; H, 6.26; N, 0.16; S, 3.08% Dextran 150k, ~22 DVS-$NH_2$, ~160 DVS-OH, and ~720$H_2O$ requires C, 39.55; H, 6.60; N, 0.16; S 3.07

Example 3

Preparation of Hexa-Methoxy-Crystal Violet Succinimidyl Ester (HMCV-1)

Synthesis of HMCV-1:

Scheme 1.

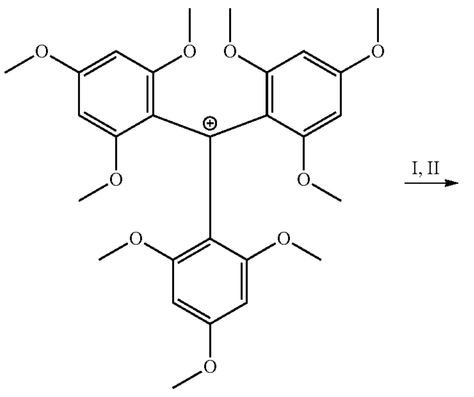

1

-continued

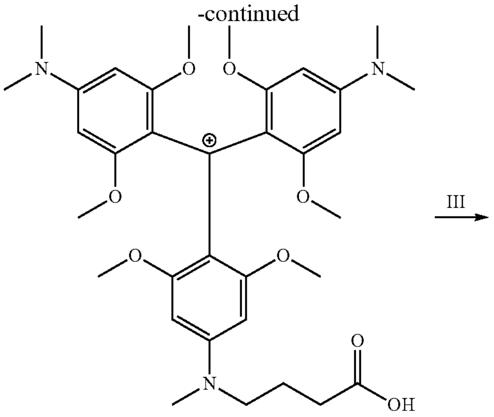

4a $C_{14}H_{46}N_3O_4^+$

Exact Mass: 624.33

Mol. Wt. (BF4-): 711

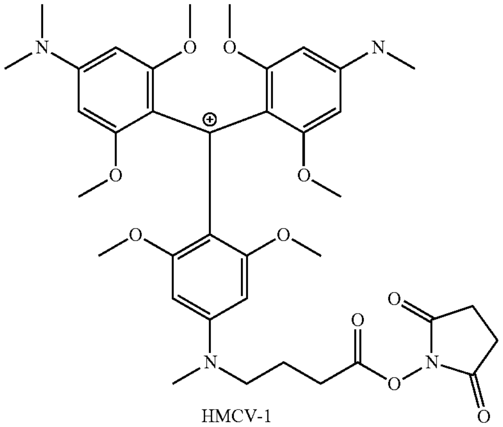

HMCV-1

$C_{38}H_{49}N_4O_{10}^+$

Exact Mass: 721.34

Mol. Wt. (Cl-): 757

I) 4-(N-methylamino)-butanic acid hydrochloride (1 eq.), Diisopropylethylamine, in acetonitrile, 20° C., 20 hours.

II) Dimethylamine (excess).

III) TSTU, Diisopropylethylamine, in acetontrile, 20° C., 2 hours.

4a ($BF_4^-$): 4-(methylamino)butyric acid hydrochloride (1.36 g; 8.8 mmol), 1 (5.0 g; 8.3 mmol), and diisopropylethylamine (5 mL) was dissolved in acetonitrile (120 mL). The reaction mixture was stirred at 30-35° C. in a dry nitrogen atmosphere for 22 h. Aqueous dimethylamine (40 mL of a 40% solution) was added and the reaction mixture was stirred for four more days. Solvent and excess dimethylamine were removed in vacuo and the remaining material dissolved in chloroform. The chloroform solution was washed twice with brine and dried over $MgSO_4$ before evaporation of the solvent and reprecipitation of the product from $CH_2Cl_2$/ether. Yield: 4.4 g (70%) of a dark blue powder.

MS (FAB+): m/z 624 (M+)

$^1$H-NMR (400 MHz, DMSO-$d_6$): δ 8.34 (1H, bs), 6.03 (2H, s), 5.83 (4H, s), 3.49 (2H, m), 3.46 (6H, s), 3.44 (12H, s), 3.12 (3H, s (masked)), 3.08 (12H, s), 1.94 (2H, t), 1.70 (2H, m).

HMCV-1 ($Cl^-$): TSTU (2-succinimido-1,1,3,3-tetramethyluronium tetrafluoroborate; 0.8 g, 2.6 mmol) was added to a solution of 4a (0.9 g, 1.26 mmol) and diisopropylethylamine (0.55 g, 4.5 mmol) in acetonitrile (15 mL). The reaction mixture was stirred in a closed flask for 2 h, before it was poured into an ice-cold nearly sat. NaCl solution (approx. 150 mL) acidified with HCl-aq (4 mL, 2 M). The water phase was extracted with chloroform (2×150 mL). The combined chloroform phases was washed with brine (2×50 mL) and dried over $MgSO_4$. Evaporation of the solvent and reprecipitation from $CH_2Cl_2$/ether gave a dark blue powder (0.80 g, 84%).

MS (FAB+): m/z 721 (M+)

$^1$H-NMR $^1$H-NMR br. (400 MHz, DMSO-$d_6$): δ 5.88 (2H, s), 5.85 (4H, s), 3.60 (2H, s), 3.46 (12H, s), 3.45 (6H, s), 3.15 (12H, s), 3.12 (3H, s), 2.85 (4H, s), 2.80 (2H, t), 1.95 (2H, m).

Example 4

Staining of Dextran 70 kDa aminodextran (0.5 mmol $NH_2$/g dextran, i.e. 35 moles amine per mole dextran) prepared by an analogous method to that of Example 2 was stained in 10 mM $NaHCO_3$ pH 8.5, 150 mM NaCl with HMCV-1 (Example 3). The dye was dissolved in dry DMSO and added slowly (10 min.) to the dextran in bicarbonate buffer. Reaction was allowed to take place for 1 hour. The staining was performed with 8 times molar excess of dye. Purification was carried out by dialysis against 10 mM Tris buffer pH 7.4, 150 mM NaCl, 1.25 mM $Ca^{2+}$, 2 mM $NaN_3$. The obtained degree of labelling of the stained dextran was determined by UV spectroscopy as 7.0 dyes per dextran.

Example 5

Glucose Measurement

AF594 stained human MBL (Example 1) and HMCV1-Dextran (Example 4) were mixed in TBS buffer (same as above) to concentrations of 10 μM of both components (using concentration of MBL-AF594 carbohydrate recognition domains, CRD, each with an Mw of approx 25 kDa). The assay chemistry mixture was sucked into a hollow fibre (regenerated cellulose, diameter 0.2 mm).

Fluorescence lifetime measurements (frequency domain) were performed in a KOALA automated sample compartment (ISS, Champaign Ill.). All solutions were pre-heated to 34° C. in a water bath, and all measurements in the KOALA instrument were recorded at 34° C. The fluorescence cell containing the fibre and fibre-holder assembly was placed in the sample holder of the KOALA, and the fluorescence cell was filled with buffer containing glucose.

The measured phase was an average of at least forty phase-angle recordings. After the completion of a measurement, the fluorescence cell was emptied using a pipette, and refilled with buffer containing the next concentration of glucose. A delay of 20 minutes between measurements was introduced to allow the assay chemistry to reach equilibrium.

To generate a glucose dose-response curve, the phase was measured at 0, 5, 10, 30, 100 and 500 mM glucose. After determination of the phase-angle at 500 mM glucose the fibre was washed several times with 10 mM TRIS buffer over a time period of 60 minutes. At this point the same phase-angle was obtained as for 0 mM Glucose. This demonstrates the reversibility of the assay.

TABLE 1

Absolute phase shifts for AF594-MBL and HMCV1-Dex70. The PMT counts reflect the intensity increase of the system.

| Glc (mM) | Phase @61 MHz 10 μM/10 μM | PMT counts 10 μM/10 μM |
|---|---|---|
| 0 | 36.1 | 3230 |
| 2.5 | 36.6 | 3370 |
| 5 | 37.4 | 3590 |
| 10 | 38.0 | 4030 |
| 25 | 39.2 | 4950 |
| 50 | 40.2 | 5770 |
| 500 | 41.7 | 7220 |

Example 6

Effect of HMCV1-Dextran Molecular Weight

Example 5 was repeated using HMCV1-Dextran of molecular weight ranging from 20 kDa to 250 kDa (prepared in an analogous way to the HMCV1-Dextran used in Example 5). It was found that the highest phase shift was achieved using 110 kDa HMCV1-dextran. The results are shown in FIG. 1.

Example 7

Effect of Stained MBL:HMCV1-Dextran Ratio

Example 5 was repeated using a range of ratios of stained MBL:HMCV1-Dextran. It was discovered that a 1:4 ratio of stained MBL:HMCV1-Dextran (5 μM concentration of MBL-AF594 carbohydrate recognition domains, CRD, each with an Mw of approx 25 kDa, and 20 μM HMCV1-Dextran, molecular weight 110 kDa) gave an increased response. The results are shown in Table 2.

TABLE 2

Absolute phase shifts for AF594-MBL 1:4 HMCV1-Dex110.

| Glucose, mM | Reponse, phase shift |
|---|---|
| 0 | 0 |
| 5 | 1.4 |
| 10 | 2.6 |
| 30 | 4.8 |
| 100 | 7.5 |
| 500 | 8.1 |

Example 8

Comparison of Stability of MBL and Con A

Figure 2A:
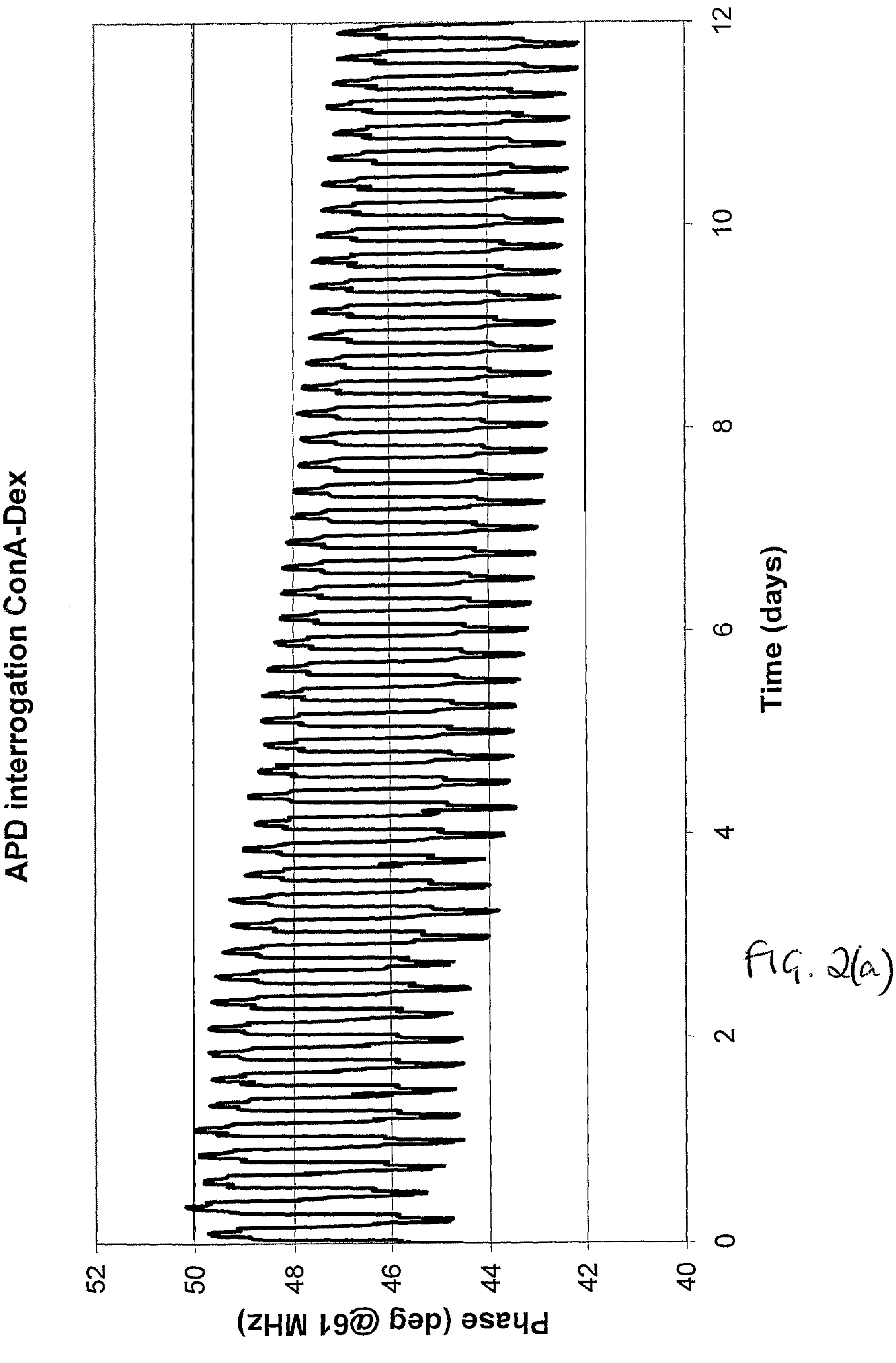
FIG. 2 shows the glucose dose response from (a) a human MBL and 110 kDa dextran assay system and (b) a Con A and 110 kDa dextran assay system (Example 8).
Figure 2B:
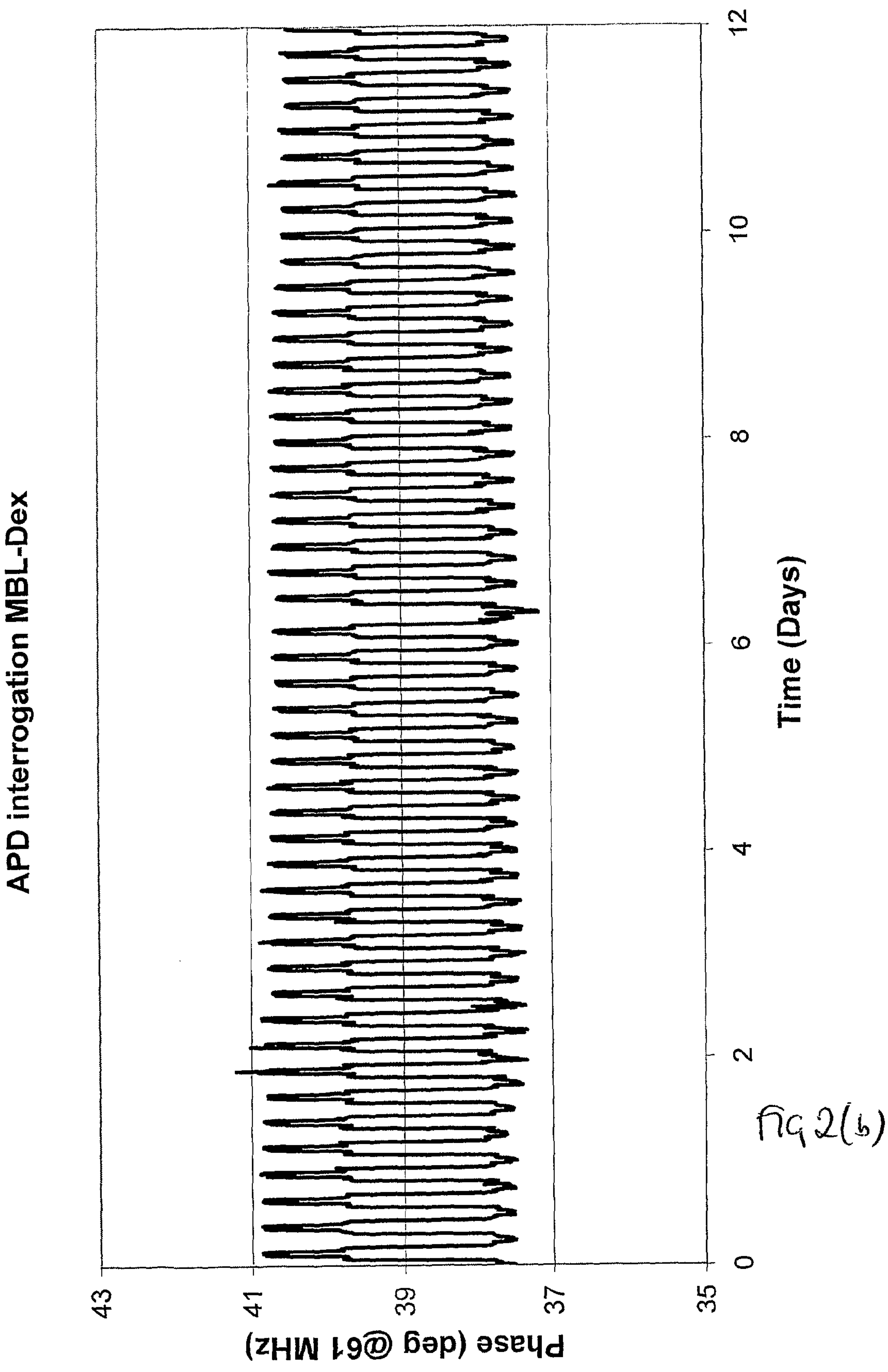

Example 5 was repeated using MBL-AF594 and ConA-AF594 as lectin with 110 kDa HMCV1-dextran as analyte analogue in physiological TRIS buffer (pH 7.4, sodium, potassium and calcium present in physiological concentrations). The glucose concentration was varied between 2.5, 5 mM, 25 mM and 50 mm in cycles over 12 days. Measurements were taken at 5 minute intervals using a miniaturized time resolved fluorimeter. In the experiment with MBL-AF594 the phase measurements at each glucose level were constant over time. A significant drift was observed in the experiment with Con A, resulting in a more than 10% reduction in the measured phase after 20 days. The results are shown in FIG. 2.

Example 9

Preparation of Aminated Periodate Oxidised Dextran 70 kDa dextran (200 mg, 0.00286 mmol) was dissolved in water (2.8 mL) and added to a 100 mM solution of sodium periodate in water (2.8 mL, 100 times molar excess). The mixture was stirred in the dark for 1 h at room temperature. The resulting mixture was transferred to a dialysis tube (MWCO 10-12 k) and dialysed over night against 5 L water.

After dialysis, the volume was adjusted to 8 ml. The periodate-oxidised dextran was split into two aliquots (4 mL, 100 mg each) and treated for a half hour with 28% aqueous ammonia (200 μL) and benzylamine (300 μL) respectively. The imine and iminium derivates were then reduced with sodium cyanoborohydride (45 mg) overnight at room temperature, and pH around 10.

The reaction mixture was dialyzed against 2×1 L 20 mM TBS the following day.

The degree of amine incorporation in the periodate oxidised dextran was determined using elemental analysis.

Example 10

Preparation of Mannosylated HSA 4 conjugates were prepared in the following way.

To 4×2 ml Eppendorf vials were each added HSA (10 mg) dissolved in a 20 mM carbonate buffer (0.4 mL, pH 9.2). p-Aminophenyl-α-D-mannopyranosyl isothiocyanate (Man-ITC) (1.6 mL) was added in 15, 30, 60, and 120 molar excess, by preparing four solutions as explained below.

Man-ITC (11.9 mg) was dissolved in DMSO (0.1 mL) and 20 mM Carbonate buffer (3.9 mL, pH 9.2). An aliquot (1.6 mL) of this solution (corresponding to 120 times molar excess) was added to an Eppendorf vial containing HSA (0.4 mL). The rest of the Man-ITC solution was diluted to double volume, and from the diluted volume, an aliquot (1.6 mL) was added to another eppendorf vial. This procedure was repeated until the four different HSA:Man-ITC mixtures had been prepared.

The four reaction mixtures were incubated in a shaker overnight at room temperature. The resulting glycoconjugates were purified on a PD-10 column. During the purification, the buffer was changed to TBS.

The degree of conjugation was determined using MALDI-TOF-MS.

TABLE 3

Determination of conjugation degree using MALDI-TOF-MS.

| | m/z (MALDI-TOF) | Number of Mannose per HSA. |
|---|---|---|
| HSA-Mannose 1:15 | 67500-70000 | 3-11 |
| HSA-Mannose 1:30 | 67700-70600 | 4-13 |
| HSA-Mannose 1:60 | 68100-72300 | 5-18 |

TABLE 3-continued

Determination of conjugation degree using MALDI-TOF-MS.

| | m/z (MALDI-TOF) | Number of Mannose per HSA. |
|---|---|---|
| HSA-Mannose 1:120 | 68600-73400 | 7-22 |

Peak width estimate was measured around half height. The number of mannose is determined using the following formula: (Peak in MS − 66500)/313

The different HSA-mannose conjugates have different affinities for MBL.

Example 11

ELLA Assay

Preparation of Biotinylated MBL

Biotin-NHS (20 μl, 7 mg/ml in DMSO, ~10-15 eq. per MBL monomer) was added to a solution of MBL (3 ml, 0.53 mg) in PBS (3 mL). The solution was gently stirred for 2 h, then transferred to a dialysis tube (MWCO 10-12K) and dialysed against TBS (2×1 L) over the course of 24 h. The resulting biotinylated MBL (0.2 mg/ml) in TBS was used without further purification.

MBL ELLA Assay

TBS buffer used in the ELLA assay is 20 mM TRIS, 150 mM NaCl, pH 7.4. 20 mM $CaCl_2$ is used where antigen is HSA-mannose and 1.25 mM $CaCl_2$ (mimicking physiological calcium concentration) is used where antigen is aminated periodate-treated dextran.

A 96-well microtitre plate was coated, overnight at 5° C., with two columns of each of the antigens (HSA-Mannose from Example 10, aminodextran, benzylamino periodate-treated dextran from Example 9) (100 μL, 20 μg/mL) in TBS. Residual binding sites were blocked by the addition of 1% (w/v) HSA in TBS (150 μL). The wells were then washed (2×200 μL TBS). Dilutions of glucose (from 100 mM to 0 mM) in biotinylated MBL prepared as described above (2 μg/mL) were added to a total volume of 100 μL. After incubation for 2 h, the plate was emptied and washed (2×200 μL TBS). Streptavidin-HRP 0.1% (v/v) (100 μL) in TBS was added. Following 1 h incubation, plates were emptied, and washed (3×200 μl TBS). The presence of HRP was visualised by the addition of substrate solution (1 mg o-phenylene dihydrochloride) and quenched after 2 min with 1 N sulphuric acid solution. Color development was determined by reading the absorbance at 490 nm, with background subtraction at 630 nm.

Figure 3:
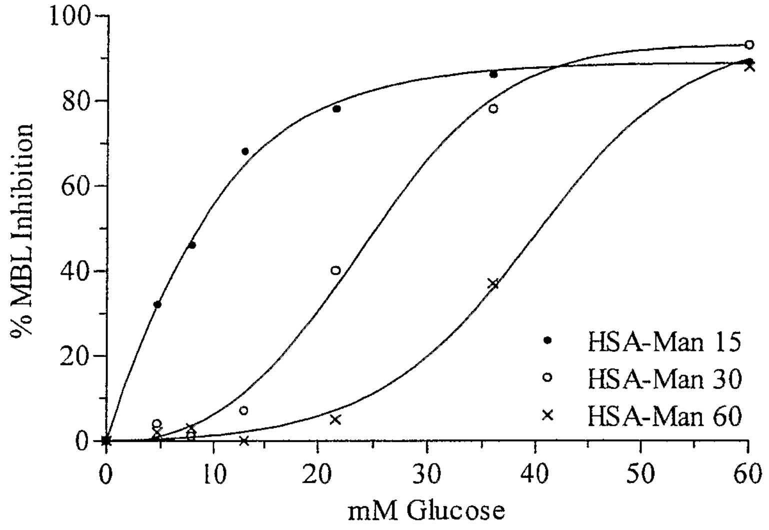
FIG. 3 shows the glucose dose response from a human MBL and HSA mannose ELLA assay system (Example 11)
Figure 4:
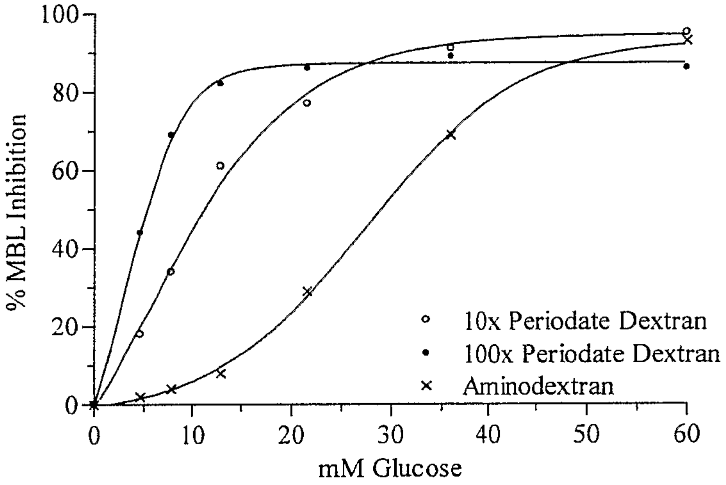
FIG. 4 shows the glucose dose response from a human MBL and periodate-treated dextran ELLA assay system (Example 11)

The results are shown in FIGS. 3 and 4.

Example 12

Co-polymer Synthesis

A water-soluble 40% Mannose copolymer was prepared by emulsion polymerisation as follows.

To a 250 ml three-necked round-bottomed flask equipped with a mechanical stirrer and a nitrogen tube was added Span80 surfactant (5.7 g; HLB [hydrophile lipophile balance] 4.3, 10% w/w based on toluene), AIBN (30 mg) and toluene (57.3 g). The flask was sealed, purged with nitrogen, and kept under a nitrogen atmosphere throughout the polymerisation. Allyl α-D-Mannopyranoside (3.52 g), 2-hydroxyethylacrylate (2.552 g), and N-(3-aminopropyl)methacrylamide hydrochloride (0.356 g) were dissolved in water (12.7 g) and filtered to remove insoluble material. This mixture was added to the vigorously stirred mixture in the round-bottomed flask through a rubber septum.

The reaction mixture was stirred at room temperature until a stable emulsion was formed (30 min), then at 60° C. for 4 h. A solution of VA-044 (1 ml, 60 mg/ml) was injected through the septum and polymerisation was continued overnight (17 h). The reaction mixture was cooled to room temperature and the emulsion was disrupted by the addition of acetone. This caused precipitation of the polymer, which was collected, redissolved in water, and precipitated by addition of acetone. The product was dried overnight under vacuum to yield 3.2 g (50%) crude light yellow polymer. Part of the crude polymer (1.0 g) was dissolved in water (10 ml), and dialysed (MWCO [molecular weight cut off] 25,000) in water to remove low molecular weight material. Freeze-drying yielded 0.46 g (46%) fluffy white polymer.

Example 13

Staining of Co-Polymer

In general the labelling of the co-polymer follows the description provided by Molecular Probes (product information MP00143, Rev. June 2001).

The co-polymer (Example 12) (88.6 mg) was dissolved in 10 mm $NaHCO_3$ solution (3 ml; pH 8.5). The polymer solution was divided equally into three Eppendorf vials. HMCV-1 (Example 3) (19.6 mg; 26.1 μmol) was dissolved in dry DMSO (600 μl). The dye was added to the polymer solutions in 10 μl aliquots every 30 seconds, in such a manner that the first vial in total received 100 μl, the second vial received 200 μl and the third vial received 300 μl. After the addition of the last aliquot, the vials were gently stirred for one hour before the solutions were dialysed (MWCO 10-12,000) in 10 mM TRIS buffer with several buffer changes and until no colour was visible in the dialysis buffer (usually 6-8 buffer changes of 500 ml and 72 hours).

Example 14

FRET Assay

Assay chemistry including stained co-polymer solution (Example 13) (4 μL) and stained MBL solution (Example 1) (8.5 μL) in 10 mM TRIS buffer (12.5 μL) was mixed and allowed to stand for at least 1 h after mixing. The assay chemistry was then transferred to a fibre as in Example 5 with a syringe. The fibre was mounted in a custom designed fibre-holder which fitted into a standard fluorescence cell (10 mm×10 mm).

Measurements were made as in Example 5 and are shown in Table 4.

TABLE 4

| Glucose, mM | Response, phase shift |
|---|---|
| 0 | 0 |
| 2.5 | 1.3 |
| 5 | 2.5 |
| 10 | 4.7 |
| 30 | 9.2 |
| 100 | 12 |
| 500 | 12.5 |

Example 15

Sensor Formulation and Implantation

Fibres were made from 1000PEGT80PBT20 polymer (prepared as described in S. Fakirov and T. Gogeva, Macromol. Chem. 191 (1990) 603-614 with a target of 80 wt % hydrophilic segment and 20 wt % hydrophobic segment) by dipping a glass rod of diameter 700 μm into a 15% w/w solution of polymer in dichloromethane (DCM) and letting it dry at room temperature. This yielded hollow fibres of outer diameter 900 μm with a lumen of diameter 700 μm. The fibre was filled with 5 μM with respect to CRD of AlexaFluor™ stained MBL (Example 1) and 20 μM of HMCV-1 stained amino-dextran 150 kDa (prepared by an analogous method to that of Example 4). Heating the polymer in order to melt it closed the fibre. The welded fibre was tested for leakage before testing and insertion.

Figure 5:
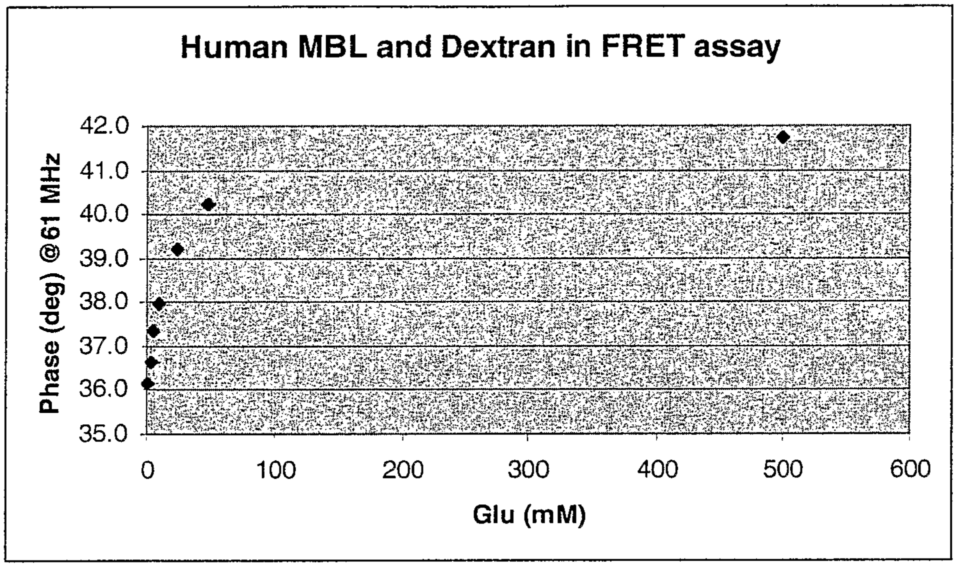
FIG. 5 shows the glucose dose response from a human MBL and 70 kDa dextran assay system (Example 15).
Figure 6:
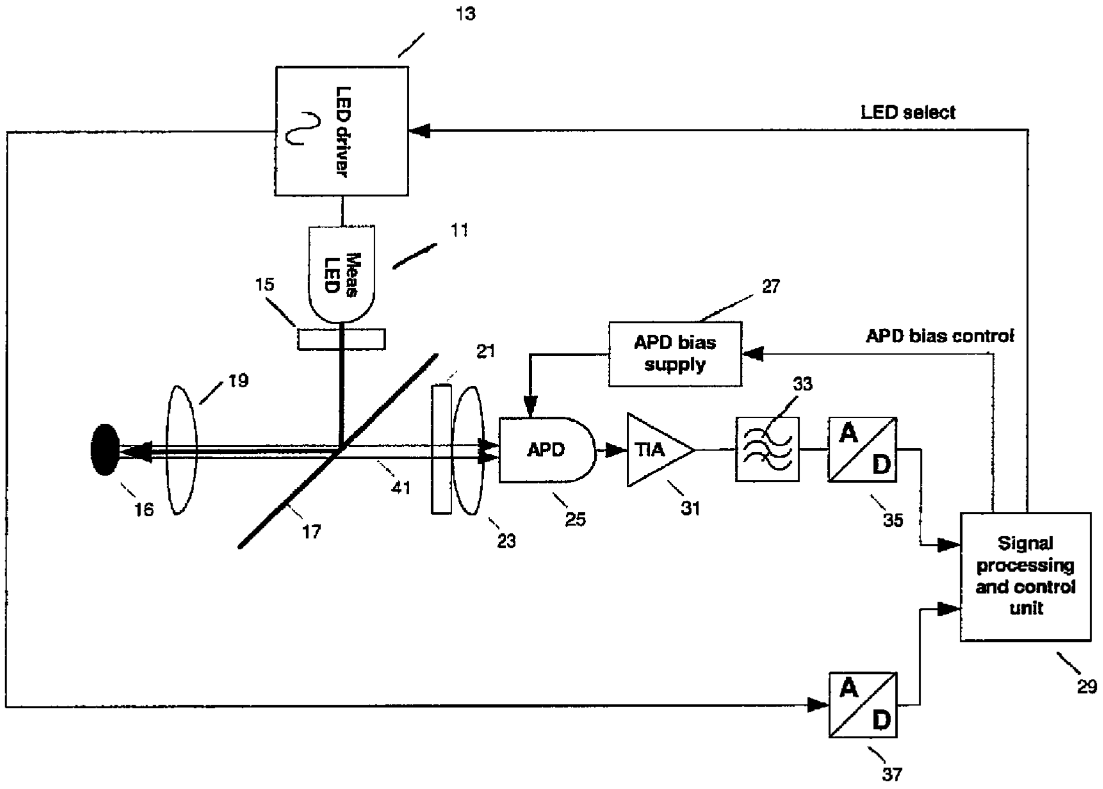
FIG. 6 shows a suitable optical set-up for interrogating the assay.

The glucose response measured by the use of time resolved fluorescence spectroscopy (frequency domain) was as shown in FIG. 5.

This type of fibre can be placed in the top of the skin by the use of a needle. A needle of suitable size (large enough to contain the wet fibre) is placed parallel to the skin surface at a depth of approx. 1 mm leaving the needle visible as a shadow through the skin. The fibre (still wet) is placed inside the needle and the needle is removed. Typically no bleeding is observed at the insertion site after the insertion procedure is completed.

When the fibre is in place the reading device is placed directly above the fibre and the measurements can begin.

The invention claimed is:

1. A sensor for the detection or measurement of carbohydrate analyte in fluid, the sensor comprising components of a competitive binding assay the readout of which is a detectable or measurable optical signal retained by a material that permits diffusion of analyte but not the assay components, the assay components comprising:

a mammalian lectin; and an analyte analogue capable of competing with analyte for binding to the lectin;

wherein the lectin is mannose binding lectin.

2. A sensor as claimed in claim 1, wherein the analyte is glucose.

3. A sensor as claimed in claim 2, wherein the analyte analogue is capable of competing with glucose at physiological calcium concentrations.

4. A sensor as claimed in claim 1, wherein the lectin is a human or humanized lectin.

5. A sensor as claimed in claim 4, wherein the lectin is derived from the human body or is a recombinant lectin.

6. A sensor as claimed in claim 1, wherein the lectin is in multimeric form.

7. A sensor as claimed in claim 1, wherein the lectin is in multimeric form, and wherein the lectin is mannose binding lectin in trimeric and/or tetrameric form.

8. A sensor as claimed in claim 1, wherein the analyte analogue comprises a plurality of carbohydrate or carbohydrate mimetic moieties.

9. A sensor as claimed in claim 8, wherein the analyte analogue comprises at least one carbohydrate moiety selected from D-fructose, D-leucrose, N-acetyl-glucosamine, D-mannose, L-fucose, N-acetyl-mannosamine, D-arabinose, myo-inositol, D-tagatose, erlose, D-glucose, D-palatinose, D-turanose, D-ribose, D-sorbitol.

10. A sensor as claimed in claim 8, wherein the analyte analogue is selected from the group consisting of polymer of carbohydrate moieties;
polymer of carbohydrate mimetic moieties;
derivatised polymer of carbohydrate moieties;
derivatised polymer of carbohydrate mimetic moieties; and
a combination thereof.

11. A sensor as claimed in claim 10, wherein the analyte analogue is selected from the group consisting of dextran, mannan, amylose, amylopectin, glycogen, hyaluronate, chondroitin, heparin, dextrin, inulin, xylan, fructan, chitin, derivatised dextran, derivatised mannan, derivatised amylose, derivatised amylopectin, derivatised glycogen, derivatised hyaluronate, derivatised chondroitin, derivatised heparin, derivatised dextrin, derivatised inulin, derivatised xylan, derivatised fructan, derivatised chitin, and a combination thereof.

12. A sensor as claimed in claim 11, wherein the analyte analogue is selected from the group consisting of dextran in which the 3- and/or 4-hydroxyl groups of at least one of the glucose units have been inactivated,
derivatised dextran in which the 3- and/or 4-hydroxyl groups of at least one of the glucose units have been inactivated, and
a combination thereof.

13. A sensor as claimed in claim 12, wherein the analyte analogue is selected from the group consisting of dextran which has been treated with periodate, derivatised dextran which has been treated with periodate, and a combination thereof.

14. A sensor as claimed in claim 11, wherein the dextran is aminated.

15. A sensor as claimed in claim 8, wherein the analyte analogue is a carbohydrate-protein conjugate or a carbohydrate-dendrimer conjugate.

16. A sensor as claimed in claim 15, wherein the analyte analogue is a carbohydrate-albumin conjugate.

17. A sensor as claimed in claim 8, wherein the analyte analogue is a flexible water-soluble non-polysaccharide polymer bearing pendant carbohydrate or carbohydrate mimetic moieties.

18. A sensor as claimed in claim 8, wherein the components of the assay are retained by a shell or matrix material.

19. A sensor as claimed in claim 18, wherein the components of the assay are retained by a shell of biodegradable material encapsulating the assay components while allowing glucose to contact the assay components, wherein the biodegradable material comprises a co-polymer having hydrophobic and hydrophilic units.

20. A sensor as claimed in claim 8, wherein the retaining material is biodegradable.

21. A sensor as claimed in claim 1, wherein the analyte analogue bears one or more energy donor or energy acceptor moieties.

22. A sensor as claimed in claim 1, wherein said detectable or measurable optical signal is generated by proximity based signal generating/modulating moieties.

23. A sensor as claimed in claim 22, wherein the lectin is labelled with one of an proximity based signal generating/modulating moiety pair and the analyte analogue is labelled with the other of the proximity based signal generating/modulating moiety pair.

24. A method of preparing a sensor as claimed in claim 1, comprising one or more of phase separation, solvent evaporation, extraction, spray drying, spray coating, spray chilling, rotary disk atomisation, fluid bed coating, coextrusion and pan coating.

25. A method of detecting glucose using a sensor as claimed in claim 1, comprising implantation of the sensor into the skin of a mammal, detection or measurement of glucose using external optical means and degradation of the biodegradable material.

26. A method of detecting glucose using a sensor as claimed in claim 1, comprising detection or measurement of glucose using external optical means by illumination of a said sensor present in or below the skin of a mammal.

27. A sensor for the detection or measurement of carbohydrate analyte in fluid, the sensor comprising components of a competitive binding assay the readout of which is a detectable or measurable optical signal retained by a material that permits diffusion of analyte but not the assay components, the assay components comprising:

an animal lectin; and
an analyte analogue capable of competing with analyte for binding to the lectin;
wherein the lectin is in multimeric form, and wherein the lectin is mannose binding lectin in trimeric and/or tetrameric form.

* * * * *